United States Patent [19]

Morrissey et al.

[11] Patent Number: 5,451,700

[45] Date of Patent: Sep. 19, 1995

[54] AMIDINO COMPOUNDS, THEIR MANUFACTURE AND METHODS OF TREATMENT

[75] Inventors: Michael M. Morrissey, Danville, Calif.; Hongsuk Suh, Cedar Knolls, N.J.

[73] Assignee: Ciba-Geigy Corporation, Ardsley, N.Y.

[21] Appl. No.: 978,004

[22] Filed: Nov. 18, 1992

Related U.S. Application Data

[63] Continuation-in-part of Ser. No. 960,211, Oct. 13, 1992, abandoned, which is a continuation of Ser. No. 714,108, Jun. 11, 1991, abandoned.

[30] Foreign Application Priority Data

Jun. 2, 1992 [EP] European Pat. Off. ............ 92810423

[51] Int. Cl.⁶ .................. C07C 237/32; A61K 31/165
[52] U.S. Cl. ..................................... 564/165; 546/226; 560/27; 564/47; 564/48; 564/91; 564/99; 564/157
[58] Field of Search .............. 564/165, 47, 48, 91, 564/99, 157; 514/620, 237.5, 330, 423, 478, 595, 596, 604, 605, 616; 544/162; 546/226; 548/539; 560/27

[56] References Cited

U.S. PATENT DOCUMENTS

| | | | |
|---|---|---|---|
| 4,034,010 | 7/1977 | Hamane et al. | 260/564 |
| 4,324,794 | 4/1982 | Tidwell et al. | 424/273 |
| 4,717,736 | 1/1988 | Rokach et al. | 514/539 |
| 4,808,604 | 2/1989 | Beck et al. | 514/381 |
| 4,889,871 | 12/1989 | Djuric et al. | 514/456 |
| 4,933,347 | 6/1990 | Tidwell et al. | 514/256 |
| 4,940,723 | 7/1990 | Tidwell et al. | 514/396 |
| 4,963,589 | 10/1990 | Tidwell et al. | 514/636 |
| 5,124,350 | 6/1992 | Djuric et al. | 514/456 |
| 5,162,361 | 11/1992 | Rosenthal et al. | 514/921 |
| 5,246,965 | 9/1993 | Main | 514/532 |

FOREIGN PATENT DOCUMENTS

| | | |
|---|---|---|
| 0150118 | 7/1985 | European Pat. Off. |
| 276064 | 7/1988 | European Pat. Off. |
| 0366066 | 5/1990 | European Pat. Off. |
| 0518818 | 12/1992 | European Pat. Off. |
| 0518819 | 12/1992 | European Pat. Off. |
| 9200011 | 1/1992 | WIPO |
| 9204311 | 3/1992 | WIPO |
| 9316036 | 8/1993 | WIPO |

OTHER PUBLICATIONS

J. Med. Chem., vol. 10, 1123 (1967).
J. Med. Chem., vol. 11, 245 (1968).
J. Med. Chem., vol. 12, 112 (1969).
J. Med. Chem., vol. 21, 1132 (1978).
J. Assoc. Aff. Anal. Chem., vol. 69, 624 (1986).
Chem. Abst., vol. 115, 788f (1991).
J. Med. Chem., vol. 16, 970 (1973).
J. Med. Chem., vol. 18, 477 (1975).
J. Med. Chem., vol. 19, 634 (1976).
NTIS Application PB90-237538 (1990).
J. Med. Chem., vol. 12, 408 (1969).
J. Med. Chem., vol. 17, 1160 (1974).

Primary Examiner—José G. Dees
Assistant Examiner—B. Frazier
Attorney, Agent, or Firm—Norbert Gruenfeld

[57] ABSTRACT

The invention relates to the compounds of the formula

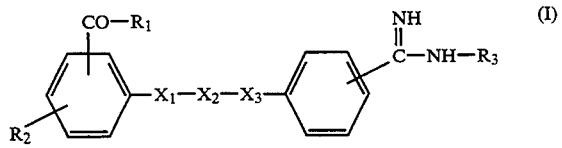

wherein the $C(=NH)-NHR_3$ group may be in tautomeric or isomeric form, and phamaceutically acceptable salts thereof. The compounds are useful as selective $LTB_4$ receptor antagonists.

24 Claims, No Drawings

AMIDINO COMPOUNDS, THEIR MANUFACTURE AND METHODS OF TREATMENT

CROSS-REFERENCES TO RELATED APPLICATIONS

This application is a continuation-in-part of application Ser. No. 960,211 filed Oct. 13, 1992 now abandoned, which is a continuation of application Ser. No. 714,108 filed Jun. 11, 1991, now abandoned.

SUMMARY OF THE INVENTION

The invention relates to the amidinophenoxyalkoxyphenyl derivatives and thio analogs as defined herein which are particularly useful as selective Leukotriene B4 (LTB4) receptor antagonists, methods for preparation thereof, pharmaceutical compositions comprising said compounds, and a method of antagonizing LTB-4 and of treating conditions or syndromes in mammals which are responsive to LTB-4 antagonism using said compounds or pharmaceutical compositions comprising said compounds of the invention.

Leukotriene $B_4$ ($LTD_4$) is an important inflammatory mediator being a potent chemotactic agent and activator of polymorphonuclear leucocytes (PMN's) and monocytes. It modulates the production and effects of other important inflammatory mediators e.g. Interleukin-1 and gamma interferon. $LTB_4$ has been implicated in the pathogenesis of a number of inflammatory diseases, such as rheumatoid arthritis, inflammatory bowel disease, psoriasis, non-steroidal-antiinflammatory-drug-induced gastropathy, adult respiratory distress syndrome (ARDS), myocardial infarction, allergic rhinitis, hemodialysis-induced neutropenia, and late phase asthma.

The compounds of the invention are useful for the treatment of the conditions mediated by $LTB_4$ which are cited above. In addition, the compounds are also useful for the treatment of pain and osteoarthritis, for the treatment of ocular conditions, such as ocular allergy and inflammation, and also for the treatment of dermatitis, such as atopic and contact dermatitis. There is a strong need in the art in finding potent antagonists of $LTB_4$ on human PMN's, especially those which are orally active. It has been found that the compounds according to the present invention exhibit significant $LTB_4$ antagonistic activity on human PMN's and are orally active.

DETAILED DESCRIPTION OF THE INVENTION

The invention relates to amidinophenoxyalkoxyphenyl derivatives and thio analogs of the formula

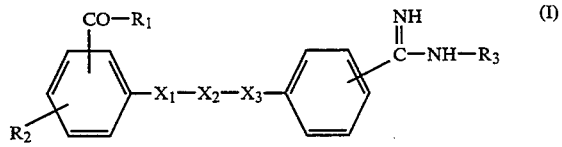
(I)

wherein the C(=NH)—NHR$_3$ group may be in tautomeric or isomeric form; and pharmaceutically acceptable salts thereof, in which:

R$_1$ is amino which is mono- or disubstituted by a substituent selected from an aliphatic hydrocarbon radical, an araliphatic hydrocarbon radical, an aromatic radical, and a cycloaliphatic hydrocarbon radical, or is amino which is disubstituted by a divalent aliphatic hydrocarbon radical or a said radical interrupted by oxygen;

R$_2$ is hydrogen, halogen, trifluoromethyl, an aliphatic hydrocarbon radical, or is hydroxy which is etherified by an aliphatic alcohol, araliphatic alcohol, or aromatic alcohol or which is esterified by an aliphatic or araliphatic carboxylic acid; or R$_2$ is hydroxy; or R$_2$ is hydroxy which is etherified by an aliphatic alcohol which is substituted by carboxy, by esterified carboxy or by amidated carboxy;

R$_3$ is hydrogen or an acyl radical which is derived from an organic carbonic acid, an organic carboxylic acid, a sulfonic acid, or a carbamic acid;

X$_1$ and X$_3$, independently of one another, are oxygen (—O—) or sulphur (—S—); and X$_2$ is a divalent aliphatic hydrocarbon radical which may be interrupted by an aromatic radical;

wherein the phenyl rings of formula I may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein aryl in the above definitions may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein a cycloaliphatic hydrocarbon radical may be substituted by an aliphatic radical; which are particularly useful as selective LTB-4 antagonists, methods for preparation thereof, pharmaceutical compositions comprising said compounds, and a method of antagonizing LTB-4 and of treating diseases in mammals which are responsive to LTB-4 antagonism using said compounds or pharmaceutical compositions comprising said compounds of the invention.

The compounds of the invention wherein the C(=NH)—NHR$_3$ group is in tautomeric or isomeric form are represented by formula I'

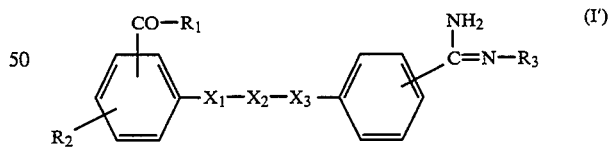
(I')

wherein R$_1$, R$_2$, R$_3$, X$_1$, X$_2$ and X$_3$ have meaning as defined for formula I.

As compounds according to the invention have a basic centre, they can thus form acid addition salts, especially pharmaceutically acceptable salts. These are formed, for example, with inorganic acids, such as mineral acids, for example sulfuric acid, a phosphoric or hydrohalic acid, or with organic carboxylic acids, such as (C$_1$–C$_4$-)alkanecarboxylic acids which, for example, are unsubstituted or substituted by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, benzoic acid or with organic sulfonic acids, such as ($C_1$–$C_4$-)alkane- or arylsulfonic acids which are unsubstituted or substituted, for example, by halogen, for example methane- or toluenesulfonic acid. Preferred are salts formed with hydrochloric acid, methanesulfonic acid and maleic acid.

The general definitions used below have, if not defined differently, the following meanings:

An aliphatic hydrocarbon radical is, for example, lower alkyl, lower alkenyl and secondarily lower alkynyl.

An araliphatic hydrocarbon radical is, for example, optionally substituted phenyl-lower alkyl and secondarily phenyl-lower alkenyl and phenyl-lower alkynyl.

A cycloaliphatic hydrocarbon radical is, for example, cycloalkyl and secondarily cycloalkenyl, which is unsubstituted or mono- or polysubstituted, for example, disubstituted, by lower alkyl.

A divalent aliphatic hydrocarbon radical is, for example, lower alkylene.

A divalent aliphatic radical interrupted by oxygen is, for example, lower alkylene interrupted by oxygen, e.g. ethylene-O-ethylene.

A divalent aliphatic hydrocarbon radical which is interrupted by an aromatic radical is, for example, lower alkylene-phenylene-lower alkylene or lower alkylene-naphthylene-lower alkylene.

An aliphatic alcohol is, for example, a lower alkanol or lower alkenol, and an araliphatic alcohol is, for example, a phenyl-lower alkanol.

An aromatic alcohol is, for example, a phenol which is unsubstituted or is further substituted such as monosubstituted, for example, disubstituted or secondarily trisubstituted.

Hydroxy which is etherified by an aliphatic or araliphatic alcohol is, for example, lower alkoxy or lower alkenyloxy and phenyl-lower alkoxy.

An aliphatic carboxylic acid is, for example, a lower alkanoic or lower alkenoic acid, and an araliphatic carboxylic acid is, for example, a phenyl-lower alkanoic acid.

Hydroxy which is esterified by an aliphatic or araliphatic carboxylic acid is, for example, lower alkanoyloxy, secondarily lower alkenoyloxy, or is phenyl-lower alkanoyloxy.

An acyl radical which is derived from an an organic carboxylic acid is, for example, lower alkanoyl, phenyl-lower alkanoyl or unsubstituted or substituted aroyl, such as benzoyl, naphthoyl, indanoyl or fluorenoyl, or heteroaroyl such as pyridylcarbonyl, thienylcarbonyl, pyrrolylcarbonyl, furanylcarbonyl, and imidazolylcarbonyl.

An acyl radical which is derived from an organic carbonic acid is, for example, alkoxycarbonyl or alkenyloxycarbonyl which in each case are unsubstituted or substituted by an aromatic radical or is cycloalkoxycarbonyl which unsubstituted or substituted by lower alkyl.

An acyl radical which is derived from a sulfonic acid is, for example, alkanesulfonyl, arylalkanesulfonyl, cycloalkanesulfonyl or arylsulfonyl.

An acyl radical which is derived from a carbamic acid is, for example, amino-carbonyl which is substituted by alkyl, arylalkyl or aryl.

An aromatic radical is, for example, unsubstituted or substituted such as monosubstituted or polysubstituted, for example, disubstituted or secondarily trisubstituted carbocyclic aryl, such as phenyl, naphthyl, indanyl or fluorenyl, or heterocyclic aryl, such as pyridyl, thienyl, pyrrolyl, furanyl, and imidazolyl.

Aryl represents preferably monocarbocyclic aryl, advantageously optionally substituted phenyl, such being phenyl or phenyl substituted by e.g. lower alkyl, lower alkoxy, halogen or trifluoromethyl.

The phenyl rings of formulae I and IA as well as aromatic radicals referred to before and hereafter are generally unsubstituted or further substituted such as monosubstituted or polysubstituted, for example disubstituted or secondarily trisubstituted, in particular, for example, by a substituent selected from the group consisting of halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy, and phenyl-lower alkanoyloxy. Preferably, the phenyl rings of formula I and IA do not exhibit any additional substitutent.

Preferred positions of the following structural elements in the corresponding phenyl ring in formula I are: positions 4 (para) or 5 (meta) for —CO—$R_1$, position 2 (ortho) or 3 (meta) for $R_2$, and position 4 (para) for —C(=NH)—NH$R_3$. The substituent $R_3$ may be located on either nitrogen of the —C(=NH)NH$_2$ grouping and both tautomeric or isomeric forms are encompassed by the instant invention.

The term "substituted by one or more substituents" refers preferably to one, two or three such substituents, advantageously one or two.

The expression "lower" means that corresponding groups and compounds in each case contain in particular not more than 7, preferably not more than 4, carbon atoms.

Halogen is, in particular, fluorine, chlorine or bromine, and furthermore includes iodine.

Lower alkyl is, in particular, $C_1$–$C_7$-alkyl and is, for example, methyl, ethyl, n-propyl, isopropyl, n-butyl, isobutyl, sec-butyl, tert-butyl and furthermore includes corresponding pentyl, hexyl and heptyl radicals. $C_1$–$C_4$-Alkyl is preferred.

Lower alkenyl is, in particular, $C_3$–$C_7$-alkenyl and is, for example, 2-propenyl or 1-, 2- or 3-butenyl. $C_3$–$C_5$-Alkenyl is preferred.

Lower alkynyl is, in particular, $C_3$–$C_7$-alkynyl and is preferably propargyl.

Phenyl-lower alkyl is, in particular, phenyl-$C_1$–$C_4$-alkyl and is preferably benzyl, 1- and 2-phenethyl, while phenyl-lower alkenyl and phenyl-lower alkynyl are, in particular, phenyl-$C_2$–$C_5$alkenyl and -alkynyl, in particular 2-phenyl-vinyl, 3-phenylallyl and 3-phenylpropargyl.

Cycloalkyl is, in particular, $C_3$–$C_7$-cycloalkyl and is, for example, cyclopropyl, cyclobutyl, cyclopentyl, cyclohexyl and cycloheptyl. Cyclopentyl and cyclohexyl are preferred.

Cycloalkenyl is, in particular, $C_3$–$C_7$-cycloalkenyl and is preferably cyclopent-2- or -3-enyl, or cyclohex-2- and -3-en-yl.

Lower alkylene e.g. in amino which is disubstituted by lower alkylene is, in particular, $C_2$–$C_6$-alkylene and is, for example, butylene, pentylene, or 2,6-butylene. Preferred is $C_4$–$C_5$-alkylene, especially pentylene.

Lower alkylene $X_2$ is, in particular, $C_2$–$C_5$-alkylene, preferably straight-chain, and is, for example, ethylene, propylene, butylene, pentylene, hexylene, heptylene and also octylene. $C_4$–$C_7$-Alkylene is preferred, especially pentylene and also butylene, hexylene or heptylene.

Lower alkylene which is interrupted by a phenyl radical ($X_2$) is, in particular, lower alkylene-phenylene-lower alkylene or lower alkylene-naphthylene-lower alkylene such as $C_2$–$C_4$-alkylene-phenylene-$C_2$–$C_4$-alkylene or $C_2$–$C_4$-alkylene-naphthylene-$C_2$–$C_4$-alkylene, preferably straight-chain, and is, for example, methylene-phenylene-methylene, 1,2-ethylene-phenylene-1,2-ethylene, such as 1,2-ethylene-1,4-phenylene-1,2-ethylene, 1,3-propylene-phenylene-1,3-propylene, such as 1,3-propylene-1,4-phenylene-1,3-propylene, or butylene-phenylene-butylene radicals, also a corresponding 1,2-ethylene-naphthylene-1,2-ethylene radical. $C_2$–$C_4$-alkylene-phenylene-$C_2$–$C_4$-alkylene or $C_2$–$C_3$-alkylenenaphthylene-$C_2$–$C_3$-alkylene is preferred, especially 1,2-ethylene-1,4-phenylene-1,2-ethylene.

Lower alkoxy is, in particular, $C_1$–$C_7$-alkoxy and is, for example, methoxy, ethoxy, n-propyloxy, iso-propyloxy, n-butyloxy, isobutyloxy, sec-butyloxy, tert-butyloxy and furthermore includes corresponding pentyloxy, hexyloxy and heptyloxy radicals. $C_1$–$C_4$-Alkoxy is preferred.

Lower alkenyloxy is, in particular, $C_3$–$C_7$-alkenyloxy and is, for example, allyloxy or but-2-en- or but-3-enyloxy. $C_3$–$C_5$-Alkenyloxy is preferred.

Phenyl-lower alkoxy is, in particular, phenyl-$C_1$–$C_4$-alkoxy, such as benzyloxy, 1- or 2-phenylethoxy, or 1-, 2- or 3-phenylpropyloxy.

Lower alkanoyloxy is, in particular, $C_2$–$C_8$-alkanoyloxy, in particular, $C_2$–$C_5$-alkanoyloxy, such as acetyloxy, propionyloxy or pivaloyoxy.

Lower alkenoyloxy is, in particular, $C_3$–$C_5$-alkenoyloxy, in particular, $C_3$–$C_5$-alkenoyloxy, such as propenoyloxy.

Phenyl-lower alkanoyloxy is, in particular, phenyl-$C_2$–$C_5$-alkanoyloxy, in particular, phenyl-$C_2$–$C_5$-alkanoyloxy, such as phenylacetyloxy, phenylpropionyloxy or phenylpivaloyloxy.

Alkoxycarbonyl is, in particular, $C_2$–$C_{12}$-alkoxycarbonyl and is, for example, methoxy-, ethoxy-, propyloxy- pivaloyloxy- or octyloxy-carbonyl. $C_2$–$C_9$-Alkoxycarbonyl is preferred.

Alkenyloxycarbonyl is, in particular, $C_3$–$C_{12}$-alkenyloxycarbonyl, for example, allyloxycarbonyl. Preferred is $C_3$–$C_5$-alkenyloxycarbonyl.

Cycloalkyloxycarbonyl is, in particular, $C_3$–$C_7$-cycloalkoxycarbonyl, preferred is cyclopentyloxycarbonyl or cyclohexyloxycarbonyl.

Alkanesulfonyl is, in particular, $C_1$–$C_7$alkanesulfonyl and is, for example, methane-, ethane-, n-propane- or isopropanesulfonyl. $C_1$–$C_4$-Alkanesulfonyl is preferred.

Arylalkanesulfonyl is, in particular, phenyl-$C_1$-$C_7$alkanesulfonyl, for example, benzyl- or 1- or 2-phenylethan-sulfonyl. Phenyl-$C_1$–$C_7$-alkane-sulfonyl is preferred.

Cycloalkanesulfonyl is, in particular, $C_3$–$C_7$-cycloalkanesulfonyl, preferred is cyclopentanesulfonyl or cyclohexanesulfonyl.

Naphthyl is 1- or 2-naphthyl.

Indanyl is, for example, 1-, 2-, 3- or 4-indanyl.

Fluorenyl is, for example, 1-, 2-, 3-, 4- or 5-fluorenyl.

Lower alkanoyl is, in particular, $C_1$–$C_7$-alkanoyl and is, for example, formyl, acetyl, propionyl, butyryl, isobutyryl or pivaolyl. $C_2$–$C_5$-Alkanoyl is preferred.

Phenyl-lower alkanoyl is, in particular, phenyl-$C_2$–$C_7$-alkanoyl and is, for example, phenylacetyl or 2- or 3ophenylpropionyl. Phenyl-$C_2$–$C_4$-alkanoyl is preferred.

Substituted aroyl represents aroyl, such as benzoyl, which is substituted e.g. by lower alkoxy, lower alkyl, hydroxy, hydroxymethyl or by acyloxymethyl (such as lower alkanoyloxymethyl or benzoyloxymethyl.

Naphthoyl is 1- or 2-naphthoyl.

Indanoyl is, for example, 1-, 2-, 3- or 4-indanoyl.

Fluorenoyl is, for example, 1-, 2-, 3-, 4- or 5-fluorenoyl.

Esterified carboxyl represents preferably lower alkoxycarbonyl or aryl-lower alkoxycarbonyl.

Amidated carboxyl represents preferably aminocarbonyl, mono- or di-lower alkylaminocarbonyl, (mono-aryl-mono-lower alkyl)aminocarbonyl, mono- or di-(aryl-lower alkyl)aminocarbonyl or (mono-aryl-lower alkyl-mono-lower alkyl)aminocarbonyl.

The compounds of the invention exhibit valuable pharmacological properties in mammals, and are particularly useful as selective Leukotriene $B_4$ ($LTB_4$) receptor antagonists, e.g. for the treatment of a condition or syndrome in a mammal responsive to the selective antagonism of $LTB_4$ receptors, such as rheumatoid arthritis, inflammatory bowel disease, psoriasis, non-steroidal-antiinflammatory-drug-induced gastropathy, adult respiratory distress syndrome (ARDS), myocardial infarction, allergic rhinitis, hemodialysis-induced neutropenia, and late phase asthma. The compounds of the invention are also useful as analgesics for the treatment of pain of any origin, and for the treatment of osteoarthritis, also for the treatment of ocular conditions, such as ocular allergy and inflammation, and also for the treatment of dermatitis, e.g. atopic and contact dermatitis.

The above-cited properties are demonstrable in in vitro and in vivo tests, using advantageously mammals, e.g. rats. Said compounds can be applied in vitro in the form of solutions, e.g. preferably aqueous solutions, and in vivo either enterally or parenterally, advantageously orally, e.g. as a suspension or in aqueous solution. The dosage in vitro may range between about 0.5 ng/ml and about 100 ng/ml. The dosage in vivo may range, depending on the route of administration, between about 1 and about 1000 mg/kg per day.

Beneficial effects are evaluated in pharmacological tests generally known in the art, e.g. as illustrated herein.

Receptor Binding with [$^3$H]-$LTB_4$ to Intact Human Neutrophils

Neutrophils (PMN's) are prepared from uncoagulated human venous blood. Blood is dispersed into 50 ml polypropylene tubes containing 15 ml of HESPAN (Dupont, Wilmington, Del.), and mixed. Tubes are allowed to stand at room temperature for 40 minutes until most of the red blood cells sediment. The supernalants are removed and centrifuged for 5–10 rain at 400×g. The remaining pellets are diluted in 70 ml of Phosphate Buffered Saline without calcium and magnesium (PBS without metals; GIBCO, Grand Island, N.Y.) and 35 ml of this suspension are placed in each of two polypropylene tubes containing 15 ml of Ficoll-Paque (Sigma, St. Louis, Mo.). Gradients are then centrifuged for 15 minutes at 420×g. The mononuclear cell layer is discarded and the remaining red blood cell pellet is resuspended in 10 ml of PBS without metals. Twenty ml of filtered deionized water are added to the suspension for approximately 20 sec followed by the same volume of buffer at two times the normal concentration. The cell suspension is mixed and centrifuged for 5 min at 200×g, followed by one wash with buffer, and final resuspension.

Binding of [$^3$H]LTD$_4$ to LTB$_4$ receptors is measured in intact human polymorphonuclear leukocytes, as described by Gorman and Lin (Gorman, R. and Lin, A Methods Enzymol. 141: 372–378, 1987). Intact human neutrophils are suspended in Hank's Balanced Salt Solution (HBSS) at a concentration of 3×106 cells/assay tube. An aliquot of the cell suspension (300 μl) is added to triplicate tubes containing 50 μl [3H]LTB$_4$ (specific activity 32 Ci/mmol, DuPont-NEN, Boston, Mass.) at a final concentration of 0.5 nM, 100 μl buffer and 50 μl drug or buffer. Nonspecific binding is determined in the presence of 300 nM LTB$_4$. The reaction is initiated by addition of cell suspension and continued at 0° C. for 20 min. Bound radioactivity is isolated by vacuum filtration through Whatman GF/C glass fiber filters using a Brandel cell harvester and unbound radioactivity removed with 2×5 ml washes with ice-cold saline. Filters are placed in polyethylene scintillation mini-vials to which is added 3.5 ml of Formula-989 scintillation cocktail (NEN). After equilibration, radioactivity determinations and data calculations are performed using non-linear regression analysis on RS/1.

LTB$_4$-Induced PMN Aggregation

Human PMNs are prepared as previously described. Neutrophil aggregation is assessed by monitoring the intensity of light passing through a suspension of cells (Craddock et al., J. Clin. Invest. 60: 260–264, 1977) using a Payton dual channel aggregometer (model 300BD). Cuvettes containing 0.25 ml of cell suspension (25×106 cells/ml) in PBS without calcium and magnesium are incubated with 5 μg/ml ml of cytochalasin B for 2 minutes at 37° C. 5 μl of 2 μM LTB$_4$ in PBS (20 nM final concentration) are added and the aggregation response monitored for 3–5 min, the time required for optimal response, Compounds are solubilized in 0.01M DMSO and then diluted in PBS to 0.001 M. 5 μl of compound solution is added along with cytochalasin B and cells as described above. Following the preincubation period 5 μl of 2 μM LTB$_4$ are added and aggregation is measured. Percent inhibition of aggregation is calculated by comparing peak heights in the presence and absence of compound. Percent inhibition is plotted as a function of the log concentration of compound and the IC$_{50}$ determined directly from the graph.

LTD$_4$-Induced Neutropenia in the Rat

Male Sprague Dawley rats (crl: CDBR; Charles River, Wilmington, Mass.) (250–300 grams) are fasted overnight prior to the experiment. At least six animals are used per treatment group. Rats are given vehicle or compound either intravenously or orally and at intervals after dosing, neutrophil counts are determined from blood samples obtained just prior to and 20 seconds after intravenous infusion of 200 ng LTB$_4$. In studies where compound is administered orally, drug is given by gavage. When drug is administered intravenously, rats are first anesthetized with 50 mg/kg i.p. of Sodium Pentabarbital. The jugular vein is exposed and cleaned of the surrounding tissue. At 3, 4 or 18 hours following administration of compound or vehicle by either route, blood samples are taken (0.3 ml of blood in 1.5 ml polypropylene microcentrifuge tube containing 0.01 ml 7.5% EDTA). Blood neutrophil counts are determined using a Technicon H-1 hematology instrument. Antagonism of the LTD$_4$-induced neutropenia response for the compounds tested is calculated.

Analgesic activity can be demonstrated e.g. in the Randall-Selitto test for analgesia, e.g. as described in Arch. Int. Pharmacodyn. Ther. 111,409 (1957).

Antiinflammatory activity can be demonstrated by measuring the inhibition of the edema and inhibition of the influx of polymorphonuclear (PMN's) and mononuclear leukocytes (monocytes and macrophages) after oral administration in the rat model in which pleurisy is first induced by injecting carrageenin into the pleural cavity, e.g. according to A. P. Almeida et al., J. Pharmacol. Exp. Therap. 214, 74 (1980), in particular during the late phase of the carrageenin-induced pleurisy.

Bronchial effects such as anti-asthmatic activity, can be demonstrated in the antigen-induced guinea pig bronchoconstriction test, e.g. as described by Anderson et al, Br. J. Pharmacol. 1983, 78, 67–74.

The trinitrobenzenesulfonic acid-induced chronic colitis test in the rat, e.g. as described by Wallace et al, Gastroenterology 1989, 96, 29–36, can be used to evaluate compounds for effects indicative of utility in inflammatory bowel diseases.

The arachidonic acid-induced mouse ear edema test, e.g. as described by Young et al, J. Invest, Dermatol. 1984, 82, 367–371 can be used to evaluate compounds for effects indicative of utility in dermatological disorders such as psoriasis.

The invention especially relates to compounds of formula I and pharmaceutically acceptable salts thereof, in which:

$R_1$ is amino which is mono- or disubstituted by a substituent selected from lower alkyl, lower alkenyl, lower alkynyl, phenyl-lower alkyl, phenyl-lower alkenyl, phenyl-lower alkynyl, phenyl, naphthyl, indanyl, fluorenyl, cycloalkyl, and cycloalkenyl, cycloalkyl and cycloalkenyl each being unsubstituted or mono- or polysubstituted by lower alkyl, or is amino which is disubstituted by lower alkylene;

$R_2$ is hydrogen, halogen, trifluoromethyl, lower alkyl, lower alkenyl, lower alkynyl, lower alkoxy, lower alkenyloxy, phenyl-lower alkoxy, phenoxy, lower alkanoyloxy, lower alkenoyloxy, or phenyl-lower alkanoyloxy; or $R_2$ is hydroxy; or $R_2$ is lower alkoxy substituted by carboxy, lower alkoxycarbonyl, aminocarbonyl or mono- or di-lower alkylaminocarbonyl;

$R_3$ is hydrogen, alkoxycarbonyl or alkenyloxycarbonyl, each of which is unsubstituted or substituted by phenyl, naphthyl, indanyl or fluorenyl, or is cycloalkoxycarbonyl being unsubstituted or mono- or polysubstituted by lower alkyl, or is lower alkanoyl or phenyl-lower alkanoyl, or is benzoyl, naphthtoyl, indanoyl or fluorenoyl, or is $C_1$–$C_7$alkanesulfonyl, phenyl-$C_1$–$C_7$alkanesulfonyl, $C_3$–$C_7$-cycloalkanesulfonyl, or phenylsulfonyl, or is aminocarbonyl which is substituted by lower alkyl, phenyl-lower alkyl or phenyl;

$X_1$ and $X_3$, independently of one another, are O or S;

$X_2$ is lower alkylene, lower alkylene-phenylene-lower alkylene or lower alkylene-naphthylene-lower alkylene;

wherein the phenyl rings of formula I may be, independently of one another, substituted by one or more substituents selected from halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy and phenyl-lower alkanoyloxy;

wherein the aromatic radicals in the above definitions may be, independently of one another, substituted by one or more substituents selected from halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy and phenyl-lower alkanoyloxy.

The invention especially relates to compounds of formula I and pharmaceutically acceptable salts thereof, in which:

$R_1$ is amino which is mono- or disubstituted by a substituent selected from $C_1$–$C_7$-alkyl, phenyl-$C_1$–$C_7$-alkyl, phenyl and $C_3$–$C_6$-cycloalkyl, $C_3$–$C_6$-cycloalkyl being unsubstituted or mono- or polysubstituted by $C_1$–$C_7$-alkyl, or is amino which is disubstituted by $C_3$–$C_6$-alkylene;

$R_2$ is hydrogen, $C_1$–$C_7$-alkoxy or phenyl-$C_1$–$C_4$-alkoxy; or $R_2$ is hydroxy; or $R_2$ is $C_1$–$C_7$-alkoxy substituted by carboxy or lower alkoxycarbonyl;

$R_3$ is hydrogen, $C_1$–$C_{12}$-alkoxy-carbonyl, $C_2$–$C_5$-alkanoyl, phenyl-$C_2$–$C_5$-alkanoyl, benzoyl which is unsubstituted or substituted by halogen, trifluoromethyl, $C_1$–$C_7$-alkyl, or $C_1$–$C_7$-alkoxy, $C_3$–$C_6$-cycloalkylcarbonyl which is unsubstituted or substituted by $C_1$–$C_7$-alkyl, or is benzoyl, naphthtoyl, indanoyl or fluorenoyl, or is $C_1$–$C_7$alkanesulfonyl, phenyl-$C_1$–$C_7$alkanesulfonyl, $C_3$–$C_7$-cycloalkanesulfonyl, or phenylsulfonyl, or is aminocarbonyl which is substituted by $C_1$–$C_7$-alkyl, phenyl-$C_1$–$C_7$-alkyl or phenyl;

$X_1$ and $X_3$ each are —O—, or furthermore are, independently of one another, —O— or —S—;

$X_2$ is $C_2$–$C_7$-alkylene or $C_2$–$C_4$-alkylene-phenylene-$C_2$–$C_4$-alkylene; wherein the phenyl rings of formula I may be unsubstituted or, furthermore, independently of one another, substituted by one or more substituents selected from halogen, trifluoromethyl, $C_1$–$C_7$-alkyl, and $C_1$–$C_7$-alkoxy;

wherein phenyl in the above definitions is unsubstituted or, furthermore, independently of one another, substituted by one or more substituents selected from halogen, trifluoromethyl, $C_1$–$C_7$-alkyl, and $C_1$–$C_7$-alkoxy.

The invention especially relates to compounds of formula I and pharmaceutically acceptable salts thereof, in which —CO—$R_1$ is located in position 4 (para) or 3 or 5 (meta) of the corresponding phenyl ring with respect to —$X_1$—; $R_2$- is located in position 2 (ortho) or 3 (meta) of the corresponding phenyl ring with respect to —$X_1$—; and —C(=NH)—NHR$_3$ is located in position 4 (para) of the corresponding phenyl ring with respect to —$X_3$—.

The invention especially relates to compounds of formula IA

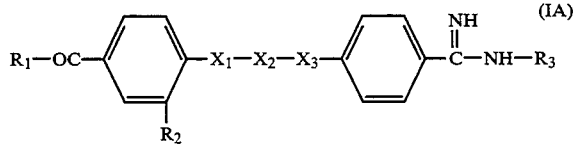

wherein the C(=NH)—NHR$_3$ group may be in tautomeric or isomeric form, and pharmaceutically acceptable salts thereof, in which:

$R_1$ is di-$C_1$–$C_4$-alkylamino, such as di-ethylamino or di-isopropylamino, $C_1$–$C_4$alkyl-phenylamino, such as phenyl-isopropyl-amino, $C_1$–$C_4$alkyl-(phenyl-$C_1$–$C_4$-alkyl)-amino, such as methyl-benzyl-amino, di-$C_3$–$C_6$-cycloalkylamino, such as di-cyclohexylamino, which is unsubstituted or substituted by $C_1$–$C_4$-alkyl, or 1-piperidino substituted by $C_1$–$C_4$-alkyl, such as 2-methyl-1-piperidino;

$R_2$ is hydrogen or $C_1$–$C_4$-alkoxy, such as methoxy; or $R_2$ is hydroxy; or $R_2$ is $C_1$–$C_4$-alkoxy $R_3$ is hydrogen, $C_1$–$C_{12}$-alkoxycarbonyl'such as methoxycarbonyl or octyloxycarbonyl, which is substituted by carboxy, lower alkoxycarbonyl, aminocarbonyl or by mono- or di-lower alkylaminocarbonyl; phenyl-$C_1$–$C_7$-alkoxycarbonyl, such as benzyloxycarbonyl, $C_2$–$C_5$-alkanoyl, such as acetyl, benzoyl which is unsubstituted or substituted by halogen, trifluoromethyl, $C_1$–$C_4$-alkyl or by $C_1$–$C_4$-alkoxy, such as 3,4-dimethoxybenzoyl, $C_3$–$C_6$-cycloalkylcarbonyl which is unsubstituted or substituted by $C_1$–$C_4$-alkyl, such as 2-isopropyl-5-methyl-cyclohexylcarbonyl;

$X_1$ and $X_3$ are —O—;

$X_2$ is $C_4$–$C_7$-alkylene, such as pentylene;

wherein the phenyl rings of formula IA may be unsubstituted or, furthermore, independently of one another, substituted by one or more substituents selected from halogen, trifluoromethyl, $C_1$–$C_4$-alkyl, and $C_1$–$C_4$-alkoxy.

The invention especially relates to compounds of formula IA and pharmaceutically acceptable salts thereof, in which:

$R_1$ is di-$C_1$–$C_4$-alkylamino, such as di-ethylamino or di-isopropylamino, $C_1$–$C_4$-alkyl-(phenyl)-amino, such as phenyl-isopropyl-amino, $C_1$–$C_4$-alkyl-(phenyl-$C_1$–$C_4$-alkyl)-amino, such as methyl-benzyl-amino, di-$C_3$–$C_6$-cycloalkylamino, such as dicyclohexylamino which is unsubstituted or substituted by $C_1$–$C_4$-alkyl, or 1-piperidino substituted by $C_1$–$C_4$-alkyl, such as 2-methyl-1-piperidino;

$R_2$ is hydrogen or $C_1$–$C_4$-alkoxy, such as methoxy; or $R_2$ is hydroxy; or $R_2$ is $C_1$–$C_4$-alkoxy which is substituted by carboxy, lower alkoxycarbonyl, aminocarbonyl or mono- or di-lower alkylaminocarbonyl;

$R_3$ is $C_1$–$C_4$alkanesulfonyl, such as methane-, ethane- or isopropanesulfonyl, phenyl-$C_1$–$C_4$-alkanesulfonyl, such as benzylsulfonyl, $C_3$–$C_4$-cycloalkane-sulfonyl, such as cyclohexanesulfonyl, or phenylsulfonyl, or is aminocarbonyl which is substituted by $C_1$–$C_4$-alkyl, phenyl-$C_1$–$C_4$-alkyl or phenyl;

$X_1$ and $X_3$ are —O—;

$X_2$ is $C_4$–$C_7$-alkylene, such as pentylene.

The invention especially relates to compounds of formula IA and pharmaceutically acceptable salts thereof, in which:

$R_1$ is di-$C_1$–$C_4$-alkylamino, such as di-ethylamino or di-isopropylamino, $C_1$–$C_4$-alkyl-(phenyl)-amino, such as phenyl-isopropyl-amino, $C_1$–$C_4$-alkyl-(phenyl-$C_1$–$C_4$-alkyl)-amino, such as methyl-benzyl-amino, di-$C_3$–$C_6$-cycloalkylamino, such as dicyclohexylamino which is unsubstituted or substituted by $C_1$–$C_4$-alkyl, or 1-piperidino substituted by $C_1$–$C_4$-alkyl, such as 2-methyl-1-piperidino;

$R_2$ is hydrogen or $C_1$–$C_4$-alkoxy, such as methoxy; or $R_2$ is hydroxy or $C_1$–$C_4$-alkoxy substituted by $C_1$–$C_4$-alkoxycarbonyl, such as ethoxycarbonylmethyl, or by aminocarbonyl;

$R_3$ is hydrogen; or $R_3$ is lower alkanoyl, such as acetyl;

$X_1$ and $X_3$ are —O—;

$X_2$ is $C_4$–$C_7$-alkylene, such as pentylene.

The invention further especially relates to compounds of formula IA and pharmaceutically acceptable salts thereof, in which:

$R_1$ is di-$C_1$–$C_4$-alkylamino, such as di-isopropylamino;

$R_2$ is hydrogen or $C_1$–$C_4$-alkoxy, such as methoxy;

$R_3$ is $C_1$–$C_{12}$-alkoxycarbonyl, such as methoxycarbonyl or octyloxycarbonyl, phenyl-$C_1$–$C_4$-alkoxycarbonyl, such as benzyloxycarbonyl, $C_2$–$C_5$-alkanoyl, such as acetyl, benzoyl which is unsubstituted or substituted by halogen, trifluoromethyl, $C_1$–$C_4$-alkyl, or $C_1$–$C_4$-alkoxy, such as 3,4-dimethoxybenzoyl, $C_3$–$C_6$-cycloalkylcarbonyl which is unsubstituted or substituted by $C_1$–$C_4$-alkyl, such as 2-isopropyl-5-methyl-cyclohexylcarbonyl;

$X_1$ and $X_3$ are —O—;

$X_2$ is $C_4$–$C_7$-alkylene, especially pentylene.

The invention further especially relates to compounds of formula IA and pharmaceutically acceptable salts thereof, in which:

$R_1$ is di-$C_1$–$C_4$-alkylamino, such as di-ethylamino or di-isopropylamino;

$R_2$ is hydrogen or $C_1$–$C_4$-alkoxy, such as methoxy;

$R_3$ is hydrogen or $C_1$–$C_4$-alkanoyl, such as acetyl;

$X_1$ and $X_3$ are —O—;

$X_2$ is $C_4$–$C_7$-alkylene, especially pentylene.

The invention also particularly relates to the compounds of formula IB

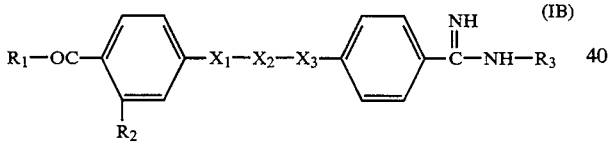

wherein the C(=NH)—$NHR_3$ group may be in tautomeric or isomeric form, and pharmaceutically acceptable salts thereof, in which:

$R_1$ is di-$C_1$–$C_4$-alkylamino, such as di-ethylamino or di-isopropylamino, $C_1$–$C_4$alkyl-(phenyl)amino, such as phenyl-isopropyl-amino, $C_1$–$C_4$-alkyl-(phenyl-$C_1$–$C_4$-alkyl)-amino, such as methyl-benzyl-amino, di-$C_3$–$C_6$-cycloalkylamino, such as dicyclohexylamino, which is unsubstituted or substituted by $C_1$–$C_4$-alkyl, or 1-piperidino substituted by $C_1$–$C_4$-alkyl, such as 2-methyl-1-piperidino;

$R_2$ is hydrogen or $C_1$–$C_4$-alkoxy, such as methoxy; or $R_2$ is hydroxy; or $R_2$ is $C_1$–$C_4$-alkoxy which is substituted by carboxy, lower alkoxycarbonyl, aminocarbonyl or by mono- or di-lower alkylaminocarbonyl;

$R_3$ is hydrogen, $C_1$–$C_{12}$-alkoxycarbonyl, such as methoxycarbonyl or octyloxycarbonyl, phenyl-$C_1$–$C_4$-alkoxycarbonyl, such as benzyloxycarbonyl, $C_2$–$C_5$-alkanoyl, such as acetyl, benzoyl which is unsubstituted or substituted by halogen, trifluoromethyl, $C_1$–$C_4$-alkyl, or $C_1$–$C_4$-alkoxy, such as 3,4-dimethoxybenzoyl, $C_1$–$C_6$-cycloalkylcarbonyl which is unsubstituted or substituted by $C_1$–$C_4$-alkyl, such as 2-isopropyl-5-methyl-cyclohexylcarbonyl;

$X_1$ and $X_3$ are —O—;

$X_2$ is $C_4$–$C_7$-alkylene, such as pentylene;

wherein the phenyl rings of formula IB may be unsubstituted or, furthermore, independently of one another, substituted by one or more substituents selected from halogen, trifluoromethyl, $C_1$–$C_4$-alkyl, and $C_1$–$C_4$-alkoxy.

The invention especially relates to compounds of formula IB and pharmaceutically acceptable salts thereof, in which:

$R_1$ is di-$C_1$–$C_4$-alkylamino, such as di-ethylamino or di-isopropylamino, $C_1$–$C_4$-alkyl-(phenyl)-amino, such as phenyl-isopropyl-amino, $C_1$–$C_4$alkyl-(phenyl-$C_1$–$C_4$-alkyl)-amino, such as methyl-benzyl-amino, di-$C_3$–$C_6$-cycloalkylamino, such as dicyclohexylamino, which is unsubstituted or substituted by $C_1$–$C_4$-alkyl, or 1-piperidino substituted by $C_1$–$C_4$-alkyl, such as 2-methyl-1-piperidino;

$R_2$ is hydrogen or $C_1$–$C_4$-alkoxy, such as methoxy; or $R_2$ is hydroxy; or $R_2$ is $C_1$–$C_4$-alkoxy which is substituted by carboxy, lower alkoxycarbonyl, aminocarbonyl or mono- or di-lower alkylaminocarbonyl;

$R_3$ is $C_1$–$C_4$alkanesulfonyl, such as methane-, ethane- or isopropanesulfonyl, phenyl-$C_1$–$C_4$-alkanesulfonyl, such as benzylsulfonyl, $C_3$–$C_7$-cycloalkanesulfonyl, such as cyclohexanesulfonyl, or phenylsulfonyl, or is aminocarbonyl which is substituted by $C_1$–$C_4$-alkyl, phenyl-$C_1$–$C_4$-alkyl or phenyl;

$X_1$ and $X_3$ are —O—;

$X_2$ is $C_4$–$C_7$-alkylene, such as pentylene.

The invention especially relates to compounds of formula IB and pharmaceutically acceptable salts thereof, in which:

$R_1$ is di-$C_1$–$C_4$-alkylamino, such as di-ethylamino or di-isopropylamino, $C_1$–$C_4$-alkyl-(phenyl)-amino, such as phenyl-isopropyl-amino, $C_1$–$C_4$alkyl-(phenyl-$C_1$–$C_4$-alkyl)-amino, such as methyl-benzyl-amino, di-$C_3$–$C_6$-cycloalkylamino, such as dicyclohexylamino, which is unsubstituted or substituted by $C_1$–$C_4$-alkyl, or 1-piperidino substituted by $C_1$–$C_4$-alkyl, such as 2-methyl-1-piperidino;

$R_2$ is hydrogen, hydroxy or $C_1$–$C_4$-alkoxy, such as methoxy; or $R_2$ is $C_1$–$C_4$-alkoxy substituted by $C_1$–$C_4$-alkoxycarbonyl, such as ethoxycarbonylmethoxy or by aminocarbonyl, such as carbamoylmethoxy;

$R_3$ is hydrogen; or $R_3$ is $C_2$–$C_5$-alkanoyl, such as acetyl;

$X_1$ and $X_3$ are —O—;

$X_2$ is $C_4$–$C_7$-alkylene, such as pentylene.

The invention further especially relates to compounds of formula IB and pharmaceutically acceptable salts thereof, in which:

$R_1$ is di-$C_1$–$C_4$-alkylamino, such as di-ethylamino or di-isopropylamino;

$R_2$ is hydrogen, hydroxy or $C_1$–$C_4$-alkoxy, such as methoxy; or $R_2$ is $C_1$–$C_4$-alkoxycarbonylmethoxy, such as ethoxycarbonylmethoxy or aminocarbonylmethoxy;

$R_3$ is hydrogen or $C_2$–$C_5$-alkanoyl, such as acetyl;

$X_1$ and $X_3$ are —O—;

$X_2$ is $C_4$–$C_7$-alkylene, especially pentylene.

The invention relates in particular to the novel compounds itemized in the examples and to the manners of preparation described therein.

The invention further relates to methods for the preparation of the compounds according to the invention. The preparation of compounds of the formula I is, for example, characterized in that, a) a compound of the formula IIa

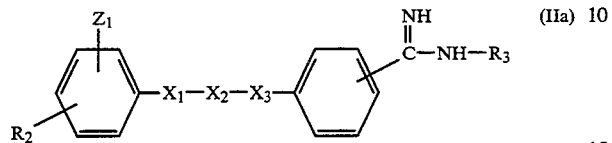

or a salt thereof in which $Z_1$ is a radical which can be convened into the variable $-CO-R_1$, $Z_1$ is converted into the variable $-CO-R_1$, or, b) for the manufacture of compounds of the formula I in which $R_3$ is hydrogen, in a compound of the formula IIIa

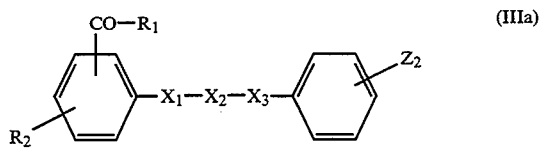

or a salt thereof in which $Z_2$ is a radical which can be convened into the variable $-C(=NH)-NH-R_3$, $Z_2$ is convened into the variable $-C(=NH)-NH-R_3$, or c) a compound of the formula IVa

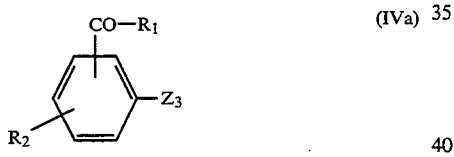

or a salt thereof is reacted with a compound of the formula IVb

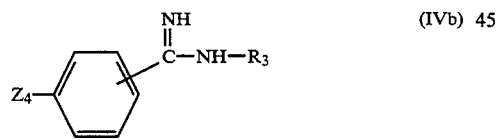

or a salt thereof in which $Z_3$ is a group of the formula $-X_1-X_2-Z_5$ and $Z_4$ is $-Z_6$, or $Z_3$ is $-Z_6$ and $Z_4$ is a group of the formula $Z_5-X_2-X_3-$, wherein one of the radicals $Z_5$ and $Z_6$ is hydroxy or mercapto and the other is hydroxy, mercapto or reactive esterified hydroxy, and, if desired, a compound of the formula I or a salt thereof obtainable according to the process or in another manner is converted into another compound or a salt thereof according to the invention, a free compound of the formula I obtainable according to the process is converted into a salt, a salt obtainable according to the process is converted into the free compound of the formula I or into another salt, or a mixture of isomers obtainable according to the process is resolved and the desired compound is isolated.

Salts of starting materials which contain at least one basic centre, for example of the formula IIa, are appropriate acid addition salts, while salts of starting materials which contain an acid group are present as salts with bases.

A radical $Z_1$ which can be convened into the variable $-CO-R_1$ is, for example, cyano, carboxy or a salt or activated carboxy.

A radical $Z_2$ which can be convened into the variable $-C(=NH)-NHR_3$ is, for example, (lower) alkoxy-iminocarbonyl or halogeno-iminocarbonyl [Halogeno—$C(=NH)$—].

Reactive esterified hydroxy (e.g. $Z_5$ or $Z_6$) is, in particular, hydroxy esterified with a strong inorganic acid or organic sulfonic acid, and is, for example, halogen, such as chlorine, bromine or iodine, sulfonyloxy, such as hydroxysulfonyloxy, halosulfonyloxy, such as, fluorosulfonyloxy, ($C_1$-$C_7$-)alkanesulfonyloxy which, if desired, is substituted, for example, by halogen, such as, methane- or trifluoromethanesulfonyloxy, ($C_5$-$C_7$-)cycloalkanesulfonyloxy, such as, cyclohexanesulfonyloxy, or benzenesulfonyloxy which, if desired, is substituted, for example by ($C_1$-$C_7$-)alkyl or halogen, such as, p-bromobenzene- or p-toluenesulfonyloxy.

The reactions described in the variants above and below are carried out in a manner known per se, for example in the absence or in the customary manner in the presence of a suitable solvent or diluent or a mixture thereof, the reaction being carried out, according to need, with cooling, at room temperature or with warming, for example in a temperature range from about −80° C. up to the boiling point of the reaction medium, preferably from about −10° C. to about +180° C., and, if necessary, in a closed vessel, under pressure, in an inert gas atmosphere and/or under anhydrous conditions.

Process a)

A compound of the formula IIa in which $Z_1$ is activated carboxy ($Z_1$) is, for example, an anhydride thereof, including a mixed anhydride, such as an acid halide, for example chloride, or an anhydride with a formic ester, an activated carboxylic ester such as cyanomethyl, (4-)nitrophenyl, polyhalogenophenyl, for example pentachlorophenyl, esters.

The reaction is, for example, carried out with an agent suitable to introduce $R_3$, for example, an amine of the formula H—$R_1$. The reaction with compounds of the formula IIa in which $Z_1$ carboxy or a salt thereof, for example, takes place under water-eliminating conditions, for example, with azeotropic removal of the water of reaction, or by treatment with a suitable condensing agent, for example, N,N'-dicyclohexyl-carbodiimide. The reaction with an activated carboxy derivative may advantageously be carried out in the presence of a base.

Suitable bases are, for example, alkali metal hydroxides, hydrides, amides, alkanolates, carbonates, triphenylmethylides, di(lower alkyl)amides, aminoalkylamides or lower alkyl silylamides, or naphthaleneamines, lower alkylamines, basic heterocycles, ammonium hydroxides, and also carbocyclic amines. Examples which may be mentioned are sodium hydroxide, sodium hydride, sodium amide, sodium (m)ethoxide, potassium tert-butoxide, potassium carbonate, lithium triphenylmethylide, lithium diisopropylamide, potassium 3-(aminopropyl)amide, potassiumbis(trimethylsilyl)amide, dimethylaminonaphthalene, di- or triethylamine, or ethyldiisopropylamine, N-methylpipefidine, pyridine, benzyltrimethylammonium hydroxide, 1,5- diazabicyclo[4.3.0]non-5-ene (DBN) and 1,8-diazabicyclo[5.4.0]undec-7-ene (DBU).

Preferably, those compounds of the formula IIa are employed in which $Z_1$ is activated carboxy. The corresponding reaction is carried out using an amine of the formula H—$R_1$. Preferred compounds of the formula IIa are corresponding acid halides such as acid chlorides or bromides derivatives thereof.

Process b)

Alkoxy-iminocarbonyl is, for example $C_1$-$C_4$alkoxy-iminocarbonyl such as methoxy- or ethoxy-iminocarbonyl, whereas halogeno-iminocarbonyl is, for example chloro-iminocarbonyl.

Preferably, those compounds of the formula IIIa are employed in which $Z_2$ is $C_1$-$C_4$alkoxy-iminocarbonyl such as methoxy- or ethoxy-iminocarbonyl. The reaction is preferably carried out by reacting with ammonia and using an acid resulting in the corresponding acid addition salt of the product. As acids are used, for example, inorganic acids, such as mineral acids, for example sulfuric acid, a phosphoric or hydrohalic acid, or with organic carboxylic acids, such as ($C_1$-$C_4$)alkanecarboxylic acids which, for example, are unsubstituted or substituted by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, benzoic acid or with organic sulfonic acids, such as ($C_1$-$C_4$)alkane- or arylsulfonic acids which are unsubstituted or substituted, for example, by halogen, for example methane- or toluenesulfonic acid. Preferred acids are hydrohalic acids, especially hydrochloric acid, organic sulfonic acids, especially methanesulfonic acid, or dicarboxylic acids, especially maleic acid.

Process c)

Preferably, those compounds of the formulae IVa and IVb are employed in which $Z_3$ is a group of the formula —$X_1$—$X_2$—$Z_5$, wherein $Z_5$ is halogen, especially bromine, and $Z_4$ is hydroxy.

The reaction is carried out preferably in the presence of a base e.g. as mentioned above, such as cesium carbonate.

The starting material can be prepared following methods known per se.

In order to prepare the starting material of the formula IIa, for example, a compound of the formula (IIb)

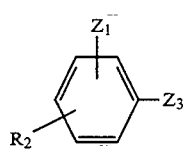

in which $Z_3$ preferably is a group of the formula —$X_1$—$X_2$—$Z_5$, wherein $Z_5$ preferably is reactive esterified hydroxy, is reacted with a compound of the formula

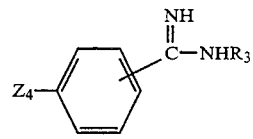

in which $Z_4$ is hydroxy or mercapto, following the method as described in process c).

If one of variables $Z_3$ and $Z_5$ represents reactive esterified hydroxy, the other preferably represents hydroxy or mercapto. A compound of the formula IVb can be obtained, for example, by convening $Z_2$ of a compound of the formula

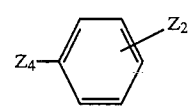

in which $Z_2$ is a radical which can be converted into the variable —C(=NH)—NH—$R_3$ following the method as described in process b). Compounds of formulae (IIb) and (IIc) are known or can be prepared according to methods known per se.

Preferably, $Z_3$ is a group of the formula $X_1$—$X_2$—$Z_5$, wherein $Z_s$ preferably is reactive esterified hydroxy, such as chlorine or bromine, and $Z_4$ is hydroxy or furthermore mercapto. A corresponding compound of the formula IIb can be obtained, for example, by reacting a compound of the formula $Z_5$—$X_2$—$Z_5$(IId) with a compound of the formula

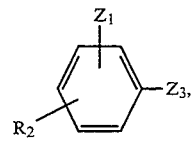

preferably in the presence of a base.

In order to prepare the starting material of the formula IIIa, $Z_1$ of a compound of the formula (IIb) is converted into radical —CO—$R_1$ following the method as described in process a) resulting in compound of the formula

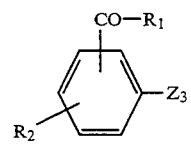

which, in the next step, is reacted with a compound of the formula (IIc) following the method as described in process c).

Relating to compounds wherein $R_2$ represents lower alkoxy substituted by carboxy, by esterified carboxy or by amidated carboxy, such compounds can be prepared from intermediates obtained by alkylation of starting materials or intermediates wherein $R_2$ is hydroxy with the appropriate reactive esterified hydroxy-substituted carboxylic acids or amides, e.g. the bromo-substituted lower alkyl carboxylic acid esters or amides. The esters can in turn be convened to the carboxylic acids or amides by methods well-known in the art. The starting materials and intermediates wherein $R_2$ is hydroxy are prepared from compounds wherein $R_2$ is e.g. methoxy by solvolysis thereof, e.g. with boron tribromide.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

A compound according to the invention which is obtainable by the process can be convened into another compound according to the invention in a manner known per se.

If one of the variables contains mono-substituted amino (for example $R_1$), corresponding compounds of the formula I or salts thereof can be N-alkylated in a manner known per se; likewise, N-mono-substituted carbamoyl (for example $R_1$) can further be N-alkylated. The (aryl-)alkylation is carried out, for example, using a reactive ester of an (aryl-)$C_1$-$C_7$-alkyl halide, for example a bromide or iodide, an (aryl-)$C_1$-$C_7$-alkylsulfonate, for example a methanesulfonate or p-toluenesulfonate, or a di-$C_1$-$C_7$-alkyl sulfate, for example dimethyl sulfate, preferably under basic conditions, such as in the presence of sodium hydroxide solution or potassium hydroxide solution, and advantageously in the presence of a phase-transfer catalyst, such as tetrabutylammonium bromide or benzyltrimethylammonium chloride, where, however, stronger basic condensing agents, such as alkali metal amides, hydrides or alkoxides, for example sodium amide, sodium hydride or sodium ethoxide, may be necessary.

If $R_3$ is hydrogen, the corresponding amidino group can be N-acylated accordingly. The acylation is carried out in a manner known per se using a suitable acylating agent. An example of a suitable acylating agent is a compound of the formula Ac—$Z_7$, where Ac denotes an acyl radical corresponding to the variable $R_3$, and $Z_7$ denotes in particular reactive activated hydroxyl. Appropriate hydroxyl can be activated, for example, by strong acids such as hydrohalic or carboxylic acid, for example by hydrochloric, hydrobromic acid, an optionally substituted, for example by halogen, alkanecarboxylic acid or by an acid of the formula Ac—OH, or by suitable activating or coupling reagents of the type detailed hereinafter, in particular in situ. Ac—$Z_7$ can furthermore represent an activated ester, where $Z_7$ denotes, in particular, cyanomethoxy, phenoxy, (4-)nitrophenoxy or polyhalogeno-, such as pentachlorophenoxy. Activating and coupling reagents which can be employed are, in particular, carbodiimides, for example N,N'-di-$C_1$-$C_4$-alkyl- or N,N'-di-$C_5$-$C_7$-cycloalkyl-carbodiimide, such as diisopropylcarbodiimide or N,N'-dicyclohexylcarbodiimide, advantageously with the addition of an activating catalyst such as N-hydroxysuccinimide or optionally substituted, for example by halogen, $C_1$-$C_7$-alkyl or $C_1$-$C_7$-alkoxy, N-hydroxy-benzotriazole or N-hydroxy-5-norbornene-2,3-dicarboxamide, furthermore $C_1$-$C_4$-alkyl halogenoformate, for example isobutyl chloroformate, suitable carbonyl compounds, for example N,N-carbonyldiimidazole, suitable 1,2-oxazolium compounds, for example 2-ethyl-5-phenyl-1,2-oxazolium 3'-sulfonate or 2-tert-butyl-5-methylisoxazolium perchlorate, suitable acylamino compounds, for example 2-ethoxy-1-ethoxycarbonyl-1,2-dihydroquinoline, or suitable phosphoryl cyanamides or azides, for example diethylphosphoryl cyanamide or diphenylphosphoryl azide, furthermore triphenylphosphine disulfide or 1-$C_1$-$C_4$-alkyl-2-halogeno-pyridinium halides, for example 1-methyl-2-chloropyridinium iodide. $Z_7$ preferably denotes halogen such as chlorine or bromine, Ac—O—, and advantageously phenoxy.

If the compounds of the formula (I), (IA) or (IB) contain unsaturated radicals, such as (lower)alkenyl groups, these can be converted into saturated radicals in a manner known per se. Thus, for example, multiple bonds are hydrogenated by catalytic hydrogenation in the presence of hydrogenation catalysts, suitable for this purpose being, for example, nickel, such as Raney nickel, and noble metals or their derivatives, for example oxides, such as palladium or platinum oxide, which may be applied, if desired, to support materials, for example to carbon or calcium carbonate. The hydrogenation may preferably carried out at pressures between 1 and about 100 at and at room temperature between about $-80°$ to about $200°$ C., in particular between room temperature and about $100°$ C. The reaction is advantageously carried out in a solvent, such as water, a lower alkanol, for example ethanol, isopropanol or n-butanol, an ether, for example dioxane, or a lower alkanecarboxylic acid, for example acetic acid.

The invention also relates to any novel starting materials and processes for their manufacture and their use.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof ,are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. Racetalc amidines (wherein $R_3$ represents hydrogen) can thus be resolved into their optical antipodes e.g. by fractional crystallization of a salt formed with an optically active acid.

Finally, the compounds of the invention are either obtained in the free form, or as a salt thereof.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to antagonize $LTB_4$ receptors, and for the treatment of a condition or syndrome responsive to the selective antagonism of $LTB_4$ receptors, comprising an effective amount of a pharmacologically active compound of the invention, alone or in combination, with one or more pharmaceutically acceptable carriers.

The novel pharmaceutical products contain, for example, from about 10% to about 80% preferably from about 20% to about 60%, of the active compound. Examples of pharmaceutical products according to the invention for enteral or parenteral administration are those in dose-unit forms such as coated tablets, tablets, capsules or suppositories, as well as ampoules. These are prepared in a manner known per se, for example using conventional mixing, granulating, coating, dissolving or freeze-drying processes. Thus, pharmaceutical products for oral use can be obtained by combining the active compound with solid excipients, where appropriate granulating a mixture which is obtained, and processing the mixture or granules, if desired or necessary, after addition of suitable auxiliaries to tablets or cores of coated tablets.

The pharmacologically active compounds of the invention are useful in the manufacture of pharmaceutical compositions comprising an effective amount thereof in conjunction or admixture with excipients or carders suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. Cores of coated tablets are provided with suitable, optionally enteric, coatings, using, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the preparation of enteric coatings, solutions of suitable cellulose products such as acetyl cellulose phthalate or hydroxypropylmethylcellulose phthalate. Colorants or pigments can be added to the tablets or coatings of coated tablets, for example, to identify or to indicate various doses of active compound. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for topical application, e.g. to the skin and eyes, are preferably aqueous solutions, ointments, creams or gels well-known in the art.

Suitable formulations for transdermal application include an effective amount of a compound of the invention with carrier. Advantageous carders include absorbable pharmacologically acceptable solvents to assist passage through the skin of the host. Characteristically, transdermal devices are in the form of a bandage comprising a backing member, a reservoir containing the compound optionally with carders, optionally a rate controlling barrier to deliver the compound of the skin of the host at a controlled and predetermined rate over a prolonged period of time, and means to secure the device to the skin.

In conjunction with another active ingredient, a compound of the invention may be administered either simultaneously, before or after the other active ingredient, either separately by the same or different route of administration or together in the same pharmaceutical formulation.

The invention further particularly relates to a method for the treatment of a condition or syndrome responsive to the selective antagonism of $LTB_4$ receptors, such as rheumatoid arthritis, inflammatory bowel disease, psoriasis, non-steroidal-antiinflammatory-druginduced gastropathy, adult respiratory distress syndrome (ARDS), myocardial infarction, allergic rhinitis, hemodialysis-induced neutropenia, and late phase asthma; also for the treatment of osteoarthritis, of pain and of ocular allergies and inflammations; and also for the treatment of atopic and contact dermatitis.

The dosage of active compound administered is dependent on the species of warmblooded animal (mammal), the body weight, age and individual condition, and on the form of administration. A unit dosage for oral administration to a mammal of about 70 kg may contain e.g. between about 1 and about 1000 mg/kg per day of the active ingredient.

The following examples are intended to illustrate the invention and are not to be construed as being limitations thereon. Temperatures are given in degrees Centrigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR). Abbreviations used are those conventional in the art.

The compounds wherein $R_3$ is not hydrogen have been assigned the isomeric structure in which $R_3$ is located on the imino (C=N) nitrogen of the amidine group; however, such may also exist in the isomeric form in which $R_3$ is on the amino nitrogen of the amidine group.

EXAMPLE 1

A stirred, 0° C. solution of ethyl 4-[5-[2-methoxy-4-[N,N-bis(1-methylethyl)aminocarbonyl]phenoxy]pentoxylbenzenecarboximidoate (420 mg, 0.87 mmol) in 20 mL anhydrous ethanol is treated with anhydrous hydrogen chloride gas for 5 minutes. After warming to room temperature, the resulting solution is concentrated in vacuo, redissolved in chloroform (20 mL) and reconcentrated. The resulting hydrochloride salt is then dissolved in ethanol (40 mL), transferred to a pressure tube and treated with anhydrous ammonia for 10 minutes at 0° C. The pressure tube is sealed and heated to 100° C. for 45 minutes. Upon cooling and concentrating in vacuo, the resulting material is purified by chromatography on silica gel (15 g) with 3–20% methanol/dichloromethane as the eluent to afford 4-[5-[4-(aminoiminomethyl)phenoxy]pentoxy]-3-methoxy-N,N-bis(1-methylethyl)benzamide monohydrochloride as a colorless foam:

CHN calculated for $C_{26}H_{38}N_3O_4Cl$—1.0 $H_2O$; Theory: % C: 61.22; % H: 7.91; % N: 8.24; Found: % C: 61.48; % H: 7.57; % N: 8.22.

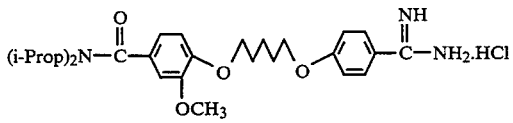

(i-Prop = isopropyl)

The starting material, ethyl 4-[5-[2-methoxy-4-[N,N-bis(1-methylethyl)aminocarbonyl]phenoxy]pentoxy]-benzenecarboximidoate, can be prepared, for example, as follows:

A stirred, 0° C. solution of 4-hydroxybenzonitrile (50.7 g, 426 mmol) in 1400 mL of dichloromethane and 75 mL anhydrous ethanol is treated with anhydrous hydrogen chloride gas (110 g) over 1.5 hours. This solution is stirred a room temperature for 64 hours and the resulting solids collected and washed with 500 mL diethyl ether and 2×1000 mL of ethyl acetate. The remaining solids (60.4 g) are dissolved in 1200 mL of water and the residual solids filtered. To the filtrate is added a solution of sodium hydroxide (12.57 g) in 150 mL water. The resulting white solid is filtered and washed with water to afford ethyl 4-hydroxybenzenecarboximidoate.

A stirred solution of ethyl 4-hydroxybenzenecarboximidoate (32.0 g, 194 mmol) in 250 mL anhydrous N,N-dimethylformamide is treated with cesium carbonate (75.7 g, 232 mmol) and 1,5-dibromopentane (89.1 g, 387 mmol) and heated at 70° C. for 1.5 hours. After cooling to room temperature, the reaction is filtered and the resulting filtrate concentrated in vacuo (<1 mtorr) to afford a yellow oil (85.7 g). This material is purified by chromatography on silica gel (850 g) with 10–60% ethyl acetate/hexanes as the eluent to afford ethyl 4-[5-bromopentoxy]benzenecarboximidoate as a colorless oil.

A stirred solution of 4-hydroxy-3-methoxy-N,N-bis(1-methylethyl)benzenecarboxamide (319 mg, 1.27 mmol) in 3.5 mL anhydrous N,N-dimethylformamide is treated with cesium carbonate (435 mg, 1.33 mmol) and ethyl 4-[5-bromopentoxy]benzenecarboximidoate (400 mg, 1.27 mmol) and heated at 70° C. for 1.0 hours. After cooling to room temperature, the reaction is partitioned between ethyl acetate and water and the organics washed with brine, dried over sodium sulfate and concentrated in vacuo to afford a yellow oil. This material is purified by chromatography on silica gel (22 g) with 30–75% ethyl acetate/hexanes as the eluent to afford ethyl 4-[5-[2-methoxy-4-[N,N-bis(1-methylethyl)aminocarbonyl]phenoxy]pentoxy]benzenecarboximidoate as a colorless oil.

EXAMPLE 2

In a way analogously as described in example 1, the following compounds can be manufactured:

4-[5-[4-(aminoiminomethyl)phenoxy]pentoxy]-3-methoxy-N,N-diethylbenzamide monohydrochloride is obtained from ethyl 4-[5-[2-methoxy-4-[N,N-diethylaminocarbonyl)phenoxy]pentoxy]benzenecarboximidoate (1.25 g) as colorless foam CHN calculated for $C_{24}H_{34}N_3O_4Cl$—0.5 $H_2O$; Theory: % C: 60.94; % H: 7.46; % N: 8.88; Found: % C: 61.10; % H: 7.47; % N: 8.99.

4-[5-[4-(aminoiminomethyl)phenoxy]pentoxy]-3-methoxy-N-methylbenzamide monohydrochloride is obtained from ethyl 4-[5-[2-methoxy-4-[N-methylaminocarbonyl]phenoxy]pentoxy]benzenecarboximidoate (475 mg) as white crystals, mp=105°–108° C.

1-[4-[5-[4-(aminoiminomethyl)phenoxy]pentoxy]-3-methoxybenzoyl]piperidine monohydrochloride is obtained from ethyl 4-[5-[2-methoxy-4-(1-piperidinylcarbonyl)phenoxy] pentoxylbenzenecarboximidoate (390 mg) as a colorless foam:

CHN calculated for $C_{25}H_{34}N_3O_4Cl$; Theory: % C: 63.08; % H: 7.20; % N: 8.83; Found: % C: 63.05; % H: 6.97; % N: 8.54.

4-[5-[4-(aminoiminomethyl)phenoxy]pentoxy]-3-methoxy-N-(phenylmethyl)benzamide monohydrochloride is obtained from ethyl 4-[5-[2-methoxy-4-[N-(phenylmethyl)aminocarbonyl]phenoxy]pentoxy]benzenecarboximidoate (412 mg) as a colorless foam:

CHN calculated for $C_{27}H_{32}N_3O_4Cl$—0.5 $H_2O$; Theory: % C: 63.95; % H: 6.56; % N: 8.29; Found: % C: 64.11; % H: 6.80; % N: 8.29.

4-[5-[4-(aminoiminomethyl)phenoxy]pentoxy]-3-methoxy-N,N-di-n-propylbenzamide monohydrochloride is obtained from ethyl 4-[5-[2-methoxy-4-[N,N-dipropylaminocarbonyl]phenoxy]pentoxy]benzenecarboximidoate (1.30 g) as a colorless foam:

CHN calculated for $C_{26}H_{36}N_3O_4Cl$—0.5 $H_2O$; Theory: % C: 62.45; % H: 7.65; % N: 8.40; Found: % C: 62.56; % H: 7.78; % N: 8.66.

4-[5-[4-(aminoiminomethyl)phenoxy]pentoxy]-3-methoxy-N,N-dimethylbenzamide monohydrochloride is obtained from ethyl 4-[5-[2-methoxy-4-[N,N-dimethylaminocarbonyl]phenoxy]pentoxy]benzenecarboximidoate (474 mg) as a colorless foam:

CHN calculated for $C_{22}H_{30}N_3O_4Cl$—1.0 $H_2O$; Theory: % C: 58.21; % H: 7.11; % N: 9.25; Found: % C: 58.35; % H: 6.82; % N: 9.64.

4-[5-[4-(aminoiminomethyl)phenoxy]pentoxy]-3-methoxy-N-methyl-N-(phenylmethyl)benzamide monohydrochloride is obtained from ethyl 4-[5-[2-methoxy-4-[N-methyl-N-(phenylmethyl)aminocarbonyl]phenoxy]pentoxy]benzenecarboximidoate (550 mg) as a colorless foam:

CHN calculated for $C_{28}H_{34}N_3O_4Cl$—1.0 $H_2O$; Theory: % C: 63.45; % H: 6.85; % N: 7.93; Found: % C: 63.74; % H: 6.61; % N: 7.96.

4-[5-[4-(aminoiminomethyl)phenoxy]pentoxy 1-3-methoxy-N-ethylbenzamide monohydrochloride is obtained from ethyl 4-[5-[2-methoxy-4-[N-ethylaminocarbonyl]phenoxy]pentoxy]benzenecarboximidoate (490 mg) as a colorless foam:

CHN calculated for $C_{22}H_{30}N_3O_4Cl$—0.5 $H_2O$; Theory: % C: 59.39; % H: 7.02; % N: 9.44; Found: % C: 59.58; % H: 6.92; % N: 9.46.

4-[5-[4-(aminoiminomethyl)phenoxy]pentoxy 1-3-methoxy-N-(1,1-dimethylethyl)benzamide monohydrochloride is obtained from ethyl 4-[5-[2-methoxy-4-N-(1,1-dimethylethyl)aminocarbonyl]phenoxy]pentoxy]-benzenecarboximidoate (530 mg) as a colorless foam:

CHN calculated for $C_{24}H_{34}N_3O_4Cl$—0.5 $H_2O$; Theory: % C: 60.94; % H: 7.46; % N: 8.88; Found: % C: 60.90; % H: 7.35; % N: 8.84.

4-[5-[4-(aminoiminomethyl)phenoxy]pentoxy]-3-methoxy-N-n-propylbenzamide monohydrochloride is obtained from ethyl 4-[5-[2-methoxy-4-[N-n-propylaminocarbonyl]phenoxy]pentoxy]benzenecarboximidoate (538 mg) as a colorless foam:

CHN calculated for $C_{23}H_{32}N_3O_4Cl$—0.5 $H_2O$; Theory: % C: 60.19; % H: 7.25; % N: 9.15; Found: % C: 60.27; % H: 7.14; % N: 9.09.

1-[4-[5-[4-(aminoiminomethyl)phenoxy]pentoxy]-3-methoxybenzoyl]-2-methylpiperidine monohydrochloride is obtained from ethyl 4-[5-[2-methoxy-4-(2-methyl-1-piperidinylcarbonyl)phenoxy]pentoxy]benzenecarboximidoate (573 mg) as a colorless foam:

CHN calculated for $C_{26}H_{36}N_3O_4Cl$—0.5 $H_2O$; Theory: % C: 62.57; % H: 7.47; % N: 8.42; Found: % C: 62.55; % H: 7.17; % N: 8.32.

4-[5-[4-(aminoiminomethyl)phenoxy]pentoxy]-3-methoxybenzoyl]morpholine monohydrochloride is obtained from ethyl 4-[5-[2-methoxy-4-[1-morpholinocarbonyl]phenoxy]pentoxy]benzenecarboximidoate as a colorless foam:

CHN calculated for $C_{24}H_{32}N_3O_5Cl$—0.75 $H_2O$; Theory: % C: 58.64; % H: 6.87; % N: 8.55; Found: % C: 58.61; % H: 6.60; % N: 8.58.

1-[4-[5-[4-(aminoiminomethyl)phenoxy]pentoxy]-3-methoxybenzoyl]-N,N-diethyl-3-piperidinecarboxamide monohydrochloride is obtained from 1-[4-[5-[4-ethoxyiminomethyl)phenoxy]pentoxy]-2-methoxybenzoyl]-N,N-diethyl-3-piperidinecarboxamide (1.00 g) as a colorless foam:

CHN calculated for $C_{30}H_{42}N_4O_5Cl$—1.0 $H_2O$; Theory: % C: 60.85; % H: 7.49; % N: 9.46; Found: % C: 60.86; % H: 7.51; % N: 9.40.

1-[4-[5-[4-(aminoiminomethyl)phenoxy]pentoxy]-3-methoxybenzoyl]pyrrolidine monohydrochloride is obtained from ethyl 4-[5-[2-methoxy-4-(1-pyrrolidinylcarbonyl)phenoxy]pentoxy]benzenecarboximidoate (731 mg) as a colorless foam:

CHN calculated for $C_{24}H_{34}N_3O_4Cl$—0.75 $H_2O$; Theory: % C: 60.62; % H: 7.10; % N: 8.84; Found: % C: 60.31; % H: 6.87; % N: 8.84.

4-[5-[4-(aminoiminomethyl)phenoxy]pentoxy]-N,N-diethylbenzamide monohydrochloride is obtained from ethyl 4-[5-[4-[N,N-diethylaminocarbonyl]phenoxy]pentoxy]benzenecarboximidoate (678 mg) as a colorless foam:

CHN calculated for $C_{23}H_{32}N_3O_3Cl$—0.75 $H_2O$; Theory: % C: 61.73; % H: 7.55; % N: 9.39; Found: % C: 61.69; % H: 7.29; % N: 9.29.

3-[5-[4-(aminoiminomethyl)phenoxy]pentoxy]-N,N-diethylbenzamide monohydrochloride (327 mg) is obtained from ethyl 3-[5-[4-[N,N-diethylaminocarbonyl]phenoxy]pentoxy]benzenecarboximidoate (475 mg) as a colorless foam:

CHN calculated for $C_{23}H_{32}N_3O_3Cl$—1.25 $H_2O$; Theory: % C: 60.52; % H: 7.62; % N: 9.20; Found: % C: 60.71; % H: 7.31; % N: 9.14.

2-[5-[4-(aminoiminomethyl)phenoxy]pentoxy]-N,N-diethylbenzamide monohydrochloride is obtained from ethyl 2-[5-[4-[N,N-diethylaminocarbonyl]phenoxy]pentoxy]benzenecarboximidoate (278 mg) as a colorless foam:

CHN calculated for $C_{23}H_{32}N_3O_3Cl$—1.25 $H_2O$; Theory: % C: 60.52; % H: 7.62; % N: 9.20; Found: % C: 60.51; % H: 7.18; % N: 9.36.

4-[5-[4-(aminoiminomethyl)phenoxy]pentoxy]-N,N-dicyclohexyl-3-methoxybenzamide monohydrochloride is obtained from ethyl 4-[5-[2-methoxy-4-[N,N-dicyclohexylaminocarbonyl]phenoxy]pentoxy]benzenecarboximidoate (663 mg) as a colorless foam:

CHN calculated for $C_{32}H_{46}N_3O_4Cl$—0.75 $H_2O$; Theory: % C: 65.74; % H: 8.02; % N: 7.19; Found: % C: 65.83; % H: 7.93; % N: 7.18.

4-[5-[4-(aminoiminomethyl)phenoxy]pentoxy]-3-methoxy-N-(1-methylethyl)-N-(phenylmethyl)benzamide monohydrochloride is obtained from ethyl 4-[5-[2-methoxy-4-[N-(1-methylethyl)-N-(phenylmethyl)aminocarbonyl]phenoxy]pentoxy]benzenecarboximidoate (483 mg) as a colorless foam:

CHN calculated for $C_{30}H_{38}N_3O_4Cl$—0.75 $H_2O$; Theory: % C: 65.09; % H: 7.19; % N: 7.59; Found: % C: 65.08; % H: 6.90; % N: 7.64.

4-[5-[4-(aminoiminomethyl)phenoxy]pentoxy]-3-methoxy-N-cyclohexyl-N-(1-methylethyl)benzamide monohydrochloride is obtained from ethyl 4-[5-[3-methoxy-4-[N-cyclohexyl-N-(1-methylethyl)aminocarbonyl]phenoxy]pentoxy]benzenecarboximidoate (727 mg) as a colorless foam:

CHN calculated for $C_{29}H_{42}N_3O_4Cl$—0.5 $H_2O$; Theory: % C: 64.36; % H: 8.01; % N: 7.76; Found: % C: 64.44; % H: 7.80; % N: 7.77.

4-[5-[4-(aminoiminomethyl)phenoxy]pentoxy]-N,N-bis(1-methylethyl)benzamide monohydrochloride is obtained from ethyl 4-[5-[4-[N,N-bis(1-methylethyl)aminocarbonyl]phenoxy]pentoxy]benzenecarboximidoate (419 mg) as a colorless foam:

CHN calculated for $C_{25}H_{36}N_3O_3Cl$—1.0 $H_2O$; Theory: % C: 62.55; % H: 7.97; % N: 8.75; Found: % C: 62.20; % H: 7.57; % N: 8.68.

4-[5-[4-(aminoiminomethyl)-3-methoxyphenoxy]pentoxy]-N,N-bis(1-methylethyl)-benzamide is obtained from ethyl 4-[5-[4-1N,N-bis(1-methylethyl)aminocarbonyl]phenoxy]pentoxy]-2-methoxybenzenecarboximidoate (1.00 g) as a colorless foam:

CHN calculated for $C_{26}H_{37}N_3O_4Cl$; Theory: % C: 68.54; % H: 8.18; % N: 9.22; Found: % C: 68.18; % H: 7.82; % N: 8.82.

4-[5-[4-(Aminoiminomethyl)phenoxy]pentoxy]-N-methyl-N-phenylbenzamide monohydrochloride is obtained from ethyl 4-[5-[4-[N-methyl-N-phenylaminocarbonyl]phenoxy]pentoxy]benzenecarboximidoate as a colorless foam:

CHN calculated for $C_{26}H_{30}N_3O_3Cl$—0.75$H_2O$; Theory: % C: 64.86; % H: 6.59; % N: 8.73 Found: % C: 65.02; % H: 6.36; % N: 8.80.

4-[5-[4-(aminoiminomethyl)phenoxy]pentoxy]-N-(1-methylethyl)-N-phenylbenzamide monomethanesulfonate is obtained from ethyl 4-[5-[4-[N-(1-methylethyl)-N-phenylaminocarbonyl]phenoxy]pentoxylbenzenecarboximidoate as a colorless foam:

CHN calculated for $C_{29}H_{37}N_3SO_6$; Theory: % C: 62.68; % H: 6.71; % N: 7.56; Found: % C: 62.64; % H: 6.68; % N: 7.67.

4-[5-[4-(aminoiminomethyl)phenoxy]pentoxy]-2-chloro-N,N-bis(1-methylethyl)benzamide monohydrochloride is obtained from ethyl 4-[5-[3-chloro-4-[N,N-bis(1-methylethyl)aminocarbonyl]phenoxy]pentoxy]benzenecarboximidoate as a colorless foam, m.p. 125°–128° C.

CHN calculated for $C_{25}H_{35}N_3O_3Cl_2$—0.5 $H_2O$; Theory: % C: 59.57; % H: 7.28; % N: 8.01; Found: % C: 59.40; % H: 7.17; % N: 8.31.

4-[5-[4-(aminoiminomethyl )phenoxy]pentoxy]-2-methyl-N,N-bis(1-methylethyl)benzamide monohydrochloride is obtained from ethyl 4-[5-[3-methyl-4-[N,N-bis(1-methylethyl)aminocarbonyl]phenoxy]pentoxy]benzenecarboximidoate as a colorless foam:

CHN calculated for $C_{20}H_{37}N_3O_3$—1.0 $H_2O$; Theory: % C: 63.20; % H: 8.16; % N: 8.50; Found: % C: 63.59; % H: 8.18; % N: 8.19.

4-[5-[4-(aminoiminomethyl)phenoxy]pentoxy]-2-methoxy-N,N -bis(1-methylethyl)benzamide monohydrochloride is obtained from ethyl 4-[5-[3-methoxy-4-[N,N-bis(1-methylethyl)aminocarbonyl ]phenoxy]pentoxy]benzenecarboximidoate as a colorless foam, m.p. 130°–134° C.

CHN calculated for $C_{26}H_{38}N_3O_4Cl$—0.5 $H_2O$; Theory: % C: 62.32; % H: 7.84; % N: 8.38; Found: % C: 61.94; % H: 7.73; % N: 7.90.

4-[5-[4-(aminoiminomethyl)phenoxy]pentoxy]-2,6-dichloro-N,N-bis(1-methylethyl)benzamide monohydrochloride is obtained from ethyl 4-[5-[3,5-dichloro-4-[N,N-bis(1-methylethyl)aminocarbonyl]phenoxy]pentoxy]benzenecarboximidoate as a colorless foam:

CHN calculated for $C_{25}H_{34}N_3O_3Cl_3$—0.5 $H_2O$; Theory: % C: 55.61; % H: 6.53; % N: 7.78; Found: % C: 55.81; % H: 6.39; % N: 7.64.

4-[5-[4-(aminoiminomethyl)phenoxy]pentoxy]-2,6-dimethyl-N,N-bis(1-methylethyl)benzamide monohydrochloride is obtained from ethyl 4-[5-[3,5-dimethyl-4-[N,N-bis(1-methylethyl)aminocarbonyl]phenoxy]pentoxy]benzenccarboximidoate as a colorless foam:

CHN calculated for $C_{27}H_{40}N_3O_3Cl$—1.0 $H_2O$; Theory: % C: 63.82; % H: 8.33; % N: 8.26; Found: % C: 63.82; % H: 7.82; % N: 7.99.

4-[5-[4-(aminoiminomethyl)phenoxy]pentoxy]-3,5-dibromo-N,N-bis(1-methylethyl)benzamide monomethanesulfonate is obtained from ethyl 4-[5-[2,6-dibromo-4-[N,N-bis(1-methylethyl)aminocarbonyl]phenoxy]pentoxylbenzenecarboximidoate as a colorless foam:

CHN calculated for $C_{26}H_{37}N_3O_6SBr_2$; Theory: % C: 45.96; % H: 5.49; % N: 6.18; Found: % C: 45.86; % H: 5.53; % N: 6.10.

4-[5-[4-(aminoiminomethyl)phenoxy]pentoxy]-2-hydroxy-N,N-bis(1-methylethyl benzamide monohydrochloride is obtained from ethyl 4-[5-[3-hydroxy-4-[N,N-bis(1-methylethyl)aminocarbonyl]phenoxy]Pentoxy]benzenecarboximidoate as a colorless foam:

CHN calculated for $C_{26}H_{36}N_3O_4Cl$—1.0 $H_2O$; Theory: % C: 60.53; % H: 7.72; % N: 8.47; Found: % C: 60.57; % H: 7.31; % N: 8.06.

3-[5-[4-(aminoiminomethyl)phenoxy]pentoxy]-4-methoxy-N,N-bis(1-methylethyl)benzamide monohydrochloride, m.p. 87°–90° C.

3-[5-[4-(aminoiminomethyl)phenoxy]pentoxy]-4-methoxy-N,N-diethylbenzamide monohydrochloride, m.p. 73°–75° C.

3-[5-[4-(aminoiminomethyl)-3-chlorophenoxy]pentoxy]-N,N-bis(1-methylethyl)benzamide monohydrochloride, m.p. 72°–76° C.

4-[5-[4-aminoiminomethyl-3-hydroxyphenoxy]-N,N-bis-(1-methylethyl)benzamide hydrochloride.

EXAMPLE 3

A stirred, 0° C. solution of 4-[5-[4-(aminoiminomethyl)phenoxy]pentoxy]-3-methoxy-N,N-bis(1-methylethyl)benzamide monohydrochloride (1.9 g, 3.86 mmol) in 20 mL water is treated with 20 mL of 1.0 N aqueous sodium hydroxide. The solution is extracted sequentially with four 50 mL portions of dichloromethane. The combined organic solution is washed with brine, dried over sodium sulfate and concentrated to give 4-[5-[4-(aminoiminomethyl)phenoxy]pentoxy]-3-methoxy-N,N-bis(1-methylethyl)benzamide (1.75 g) as a colorless foam. A portion of this material (500 mg, 1.1 mmol) is dissolved in 1 mL ethanol and treated dropwise with a solution of maleic acid (127 mg) in 1 mL ethanol. Diethyl ether (10 mL) is added slowly dropwise to induce crystallization. The crystalline product is collected by filtration, washed with ether and dried to give 4-[5-[4(aminoiminomethyl)phenoxy]pentoxy]-3-methoxy-N,N-bis(1-methylethyl)benzamide (Z)-2-butenedioate (1:1 ), mp=145°–146° C.

CHN calculated for $C_{30}H_{41}N_3O_8$; Theory: % C: 63.03; % H: 7.23; % N: 7.35; Found: % C: 62.97; % H: 7.04; % N: 7.29.

EXAMPLE 4

In a way analogously as described in example 3, the following compounds can be manufactured:

4-[5-[4-(aminoiminomethyl)phenoxy]pentoxy]-3-methoxy-N,N-bis(1-methylethyl)benzamide monomethanesulfonate is obtained from 4-[5-[4-(aminoiminomethyl)phenoxy]pentoxy]-3-methoxy-N,N-bis(1-methylethyl)benzamide (500 mg) and methanesulfonic acid; mp=122°–123° C.

4-[5-[4-(aminoiminomethyl)phenoxy]pentoxy]-3-methoxy-N,N-bis(1-methylethyl)benzamide mono-2-hydroxyethanesulfonate is obtained from 4-[5-[4-(aminoiminomethyl)phenoxy]pentoxy]-3-methoxy-N,N-bis(1-methylethyl)benzamide (500 mg) and ammonium 2-hydroxyethanesulfonate; mp=118°–120° C.

EXAMPLE 5

A stirred, 0° C. solution of 4-[5-[4-(aminoiminomethyl)phenoxy]pentoxy]-3-methoxy-N,N-bis(1-methylethyl)benzamide monohydrochloride (200 mg) in 4.0 mL anhydrous methylene chloride is treated sequentially with triethylamine (0.068 mL, 0.48 mmol) and methyl chloroformate (39 mg). The solution is stirred 30 minutes, concentrated in vacuo and the resulting solids are partitioned between ethyl acetate and water. The organic layer is washed with water and brine, dried over sodium sulfate and concentrated. The resulting material is purified by chromatography on silica gel (15 g) with 70–100% ethyl acetate/hexanes as the eluent to afford 4-[5-{4-[amino(methoxycarbonylimino)methyl]phenoxy]pentoxy]-3-methoxy-N,N-bis(1-methylethyl)benzamide

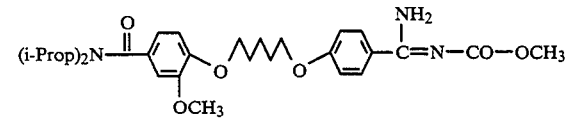

(i-Prop =isopropyl) as a colorless foam:

CHN calculated for $C_{28}H_{39}N_3O_6$; Theory: % C: 65.48; % H: 7.65; % N: 8.18; Found: % C: 65.46; % H: 7.65; % N: 8.05.

EXAMPLE 6

In a way analogously as described in example 5, the following compounds can be prepared:

4-[5-[4-[amino(phenylmethoxycarbonylimino)methyl]phenoxy]pentoxy]-3-methoxy-N,N-bis(1-methylethyl)benzamide is obtained from 4-[5-[4-(aminoiminomethyl)phenoxy]pentoxy]-3-methoxy-N,N-bis(1- methylethyl)benzamide monohydrochloride (200 mg) and benzyl chloroformate (73 mg) as a colorless foam:

CHN calculated for $C_{34}H_{43}N_3O_6$—0.5 $H_2O$; Theory: % C: 68.21; % H: 7.41; % N: 7.02; Found: % C: 68.14; % H: 7.26; % N: 6.85.

4-[5-[4-[(benzoylimino)aminomethyl]phenoxy]pentoxy]-3-methoxy-N,N-bis(1-methylethyl)benzamide is obtained from 4-[5-[4-(aminoiminomethyl)phenoxy]-pentoxy]-3-methoxy-N,N-bis(1-methylethyl)benzamide monohydrochloride (200 mg) and benzoyl chloride (61 mg) as a colorless foam:

CHN calculated for $C_{33}H_{41}N_3O_5$; Theory: % C: 70.82; % H: 7.38; % N: 7.51 Found: % C: 71.1 I; % H: 7.65; % N: 7.06.

4-[5-[4-[amino(1-oxo-3-phenyl-2-propenylimino)methyl]phenoxy]pentoxy]-3-methoxy-N,N-bis(1-methylethyl)benzamide is obtained from 4-[5-[4-(aminoiminomethyl)phenoxy]pentoxy]-3-methoxy-N,N-bis(1-methylethyl)benzamide monohydrochloride (400 mg) and cinnamoyl chloride (142 mg) as a colorless foam:

CHN calculated for $C_{35}H_{43}N_3O_5$; Theory: % C: 71.77; % H: 7.40; % N: 7.17; Found: % C: 71.95; % H: 7.60; % N: 6.91.

4-[5-[4-[amino[[[2-(1-methylethyl)-5-methylcyclohexyl]oxycarbonyl]imino]methyl]phenoxy]pentoxy]-3-methoxy-N,N-bis(1-methylethyl)benzamide is obtained from 4-[5-[4-(aminoiminomethyl)phenoxy]pentoxy]-3-methoxy-N,N-bis(1-methylethyl)benzamide monohydrochloride (300 mg) and L-menthol chloroformate (140 mg) as a colorless foam:

CHN calculated for $C_{37}H_{55}N_3O_6$; Theory: % C: 69.67; % H: 8.69; % N: 6.59; Found: % C: 70.35; % H: 8.38; % N: 6.18.

4-[5-[4-[amino[octyloxycarbonyl]imino]methyl]phenoxy]pentoxy]-3-methoxy-N,N-bis(1-methylethyl)benzamide is obtained from 4-[5-[4-(aminoiminomethyl)phenoxy]pentoxy]-3-methoxy-N,N-bis(1- methylethyl)benzamide monohydrochloride (300 mg) and octyl chloroformate (123 mg) as a colorless foam:

CHN calculated for $C_{35}H_{53}N_3O_6$; Theory: % C: 68.71; % H: 8.73; % N: 6.87; Found: % C: 68.61; % H: 8.50; % N: 6.39.

4-[5-[4-[[[9H-fluoren-9-yl)methoxycarbonyl]imino]aminomethyl]phenoxy]pentoxy]-3-methoxy-N,N-bis(1-methylethyl)benzamide is obtained from 4-[5-[4-(aminoiminomethyl)phenoxy]pentoxy]-3-methoxy-N,N-bis(1-methylethyl)benzamide monohydrochloride (300 mg) and 9-fluorenylmethyl chloroformate (166 mg) as a colorless foam:

CHN calculated for $C_{41}H_{47}N_3O_6$; Theory: % C: 72.65; % H: 6.99; % N: 6.20; Found: % C: 72.40; % H: 7.09; % N: 5.93.

4-[5-[4-[amino[(methylsulfonyl)imino]methyl]phenoxy]pentoxy]-3-methoxy-N,N-bis(1-methylethyl)benzamide is obtained from 4-[5-[4-(aminoiminomethyl)phenoxy]pentoxy]-3-methoxy-N,N-bis(1- methylethyl)benzamide monohydrochloride (300 mg) and methane sulfonyl chloride (73 mg) as a colorless foam:

CHN calculated for $C_{27}H_{39}N_3O_6S$; Theory: % C: 60.77; % H: 7.37; % N: 7.87; Found: % C: 60.85; % H: 7.55; % N: 7.66.

4-[5-[4-[amino[(phenylsulfonyl)imino]methyl]phenoxy]pentoxy 1-3-methoxy-N,N-bis(1-methylethyl)benzamide is obtained from 4-[5-[4-(aminoiminomethyl)phenoxy]pentoxy]-3-methoxy-N,N-bis(1-methylethyl)benzamide monohydrochloride (300 mg) and benzenesulfonyl chloride as a colorless foam:

CHN calculated for $C_{32}H_{41}N_3O_6S$; Theory: % C: 64.51; % H: 6.94; % N: 7.05; Found: % C: 64.73; % H: 7.17; % N: 6.86.

4-[5-[4-[amino[octyloxycarbonyl]imino]methyl]phenoxy]pentoxy]-N,N-bis(1-methylethyl)benzamide is obtained from 4-[5-[4-(aminoiminomethyl)phenoxy]pentoxy]-N,N-bis(1-methylethyl)benzamide monohydrochloride (250 mg) and octyl chloroformate (103 mg) as a colorless foam:

CHN calculated for $C_{34}H_{51}N_3O_5$; Theory: % C: 70.19; % H: 8.84; % N: 7.72; Found: % C: 70.28; % H: 8.82; % N: 7.05.

4-[5-[4-[[[2-(dimethylamino)ethyl]methylimino]carbonyl]imino]aminomethyl]phenoxy]pentoxy]-3-methoxy-N,N-bis(1-methylethyl)benzamide dihydrochloride is obtained from 4-[5-[4-(aminoiminomethyl)phenoxy]pentoxy]-3-methoxy-N,N-bis(1-methylethyl)benzamide (455 mg) and phenyl [2-(dimethylamino)ethyl]methylcarbamate (450 mg) as a colorless foam:

CHN calculated for $C_{32}It_{51}N_5O_5Cl_2-1.0 H_2O$; Theory: % C: 56.97; % H: 7.91; % N: 10.38; Found: % C: 56.64; % H: 7.83; % N: 10.10.

4-[5-[4-[[(1,1-dimethylethoxy)carbonylimino]aminomethyl]phenoxy]pentoxy]-3-methoxy-N,N-bis(1-methylethyl)benzamide is obtained from 4-[5-[4-(aminoiminomethyl)phenoxy]pentoxy]-3-methoxy-N,N-bis(1-methylethyl)benzamide monohydrochloride and t-butoxycarbonyl (BOC) anhydride, as a colorless foam:

CHN calculated for $C_{31}H_{45}N_3O6-0.5 H_2O$; Theory: % C: 65.93; % H: 8.21; % N: 7.44; Found: % C: 66.26; % H: 8.29; % N: 7.44.

4-[5-[4-[[2,2-dimethyl-1-oxopropyl)imino]aminomethyl]phenoxy]pentoxy]-3-methoxy-N,N-bis(1-methylethyl)benzamide is obtained from 4-[5-[4-(aminoiminomethyl)-phenoxy]pentoxy]-3-methoxy-N,N-bis(1-methylethyl)benzamide monohydrochloride and pivaloyl chloride as a colorless foam:

CHN calculated for $C_{31}H_{45}N_3O_5—0.5 H_2O$; Theory: % C: 68.99; % H: 8.40; % N: 7.79; Found: % C: 68.89; % H: 8.43; % N: 7.55.

4-[5-[4-[(1-oxobutylimino)aminomethyl]phenoxy]pentoxy]-3-methoxy-N,N-bis(1-methylethyl)benzamide is obtained from 4-[5-[4-(aminoiminomethyl)phenoxy]pentoxy]-3-methoxy-N,N-bis(1-methylethyl)benzamide monohydrochloride and butyryl chloride as a colorless foam:

CHN calculated for $C_{30}H_{43}N_3O_5$; Theory: % C: 68.54; % H: 8.25; % N: 7.99; Found: % C: 68.52; % H: 8.09; % N: 7.68.

4-[5-[4-[[(1-methylethoxycarbonyl)-iminolaminomethyl]phenoxy]pentoxy]-3-methoxy-N,N-bis(1-methylethyl)benzamide is obtained from 4-[5-[4-(aminoiminomethyl)phenoxy]pentoxy]-3-methoxy-N,N-bis(1-methylethyl)benzamide monohydrochloride and isopropyl chloroformate as a colorless foam:

CHN calculated for $C_{30}H_{43}N_3O_5$; Theory: % C: 66.52; % H: 8.00; % N: 7.76; Found: % C: 66.15; % H: 7.80; % N: 7.48.

4-[5-[4-[(acetylimino)aminomethyl]phenoxy]pentoxy]-3-methoxy-N,N-bis(1-methylethyl)benzamide is obtained from 4-[5-[4-(aminoiminomethyl)phenoxy]pentoxy]-3-methoxy-N,N-bis(1-methylethyl)benzamide monohydrochloride and acetyl chloride as a colorless foam:

CHN calculated for $C_{28}H_{39}N_3O_5$; Theory: % C: 67.58; % H: 7.90; % N: 8.44; Found: % C: 67.46; % H: 8.10; % N: 8.10.

EXAMPLE 7

4-[5-[4-(Aminoiminomethyl)phenoxy]pentoxy]-3-methoxy-N,N-bis(1-methylethyl)benzamide (3.65 kg, 8.01 mole) is dissolved in acetonitrile (29.2 L) with warming to 60° C. and filtered gravimetrically into a 20 gallon reactor. The product crystallizes out and is rewarmed to effect solution. A hot filtered solution of maleic acid (930 g, 8.02 mole) in acetonitrile (9.2 L) is added rapidly and an exotherm occurs to 63° C. A solid crystallizes and then redissolves. The reaction mixture is stirred to 55° C. at which point crystallization begins. The hot water bath is replaced with an ice bath and the suspension cooled to 10° C. and filtered. A second reaction mixture of the same size is run simultaneously and filtered along with the first reaction mixture. The product is washed with acetonitrile (4×2 L) and dried in vacuo (80° C., 3 mm Hg) at for 24 hours and at 83° C. for another 24 hours to give the crude product (HPLC 99.3%).

Acetonitrile (43.9 L), water (4.39 L) and 4-[5-[4-(aminoiminomethyl)-phenoxy]pentoxy]-3-methoxy-N,N-bis(1-methylethyl)benzamide (Z)-2-butenedioate (1:1) (8,780 g) are combined in a 20 gallon reactor and heated to 60° C. to effect a solution. Charcoal G-60 (440 g) is added and the reaction mixture stirred ½ hour at 60° C. and filtered gravimetrically through a heated funnel into another 20 gallon reactor. The product is allowed to crystallize at ambient temperature for 66 hours, stirred gently overnight 15 hours and filtered, washed with water (3×4 L) and dried in vacuo (85° C., 3 mm Hg) for 24 hours under a nitrogen sweep to give the pure product, 4-[5-[4-(aminoiminomethyl)phenoxy]pentoxy]-3-methoxy-N,N-bis(1-methylethyl)benzamide (Z)-2-butenedioate (1:1), mp=164°–166° C.

The starting material can be prepared, for example, as follows:

To a solution of 1-bromo-5-chloropentane (3794 g, 20.45 mol) in acetonitrile (38 L) is added 4-cyanophenol (2437 g, 20.45 mmol) and powdered powdered potassium carbonate (2827 g, 20.45 mol). This suspension is heated with stirring under nitrogen at 96° C. bath temperature (82° C.-internal) for 20 hours. Additional powdered potassium carbonate (2827 g, 20.45 mol.) is then added to the hot reaction mixture followed by potassium iodide (3397 g, 20.45 mol) and methyl vanillate (3725 g, 20.45 mol). The reaction mixture is heated under nitrogen for another 3 days until TLC shows no intermediate chloro compound present. The bath is removed and stirring stopped. The reaction mixture is filtered hot through a filter crock and into another 20 gallon reactor. The filtrate is stirred and cooled with an ice bath to 10° C. for 3 hours and the product filtered, washed with diethyl ether (4×1 L) and dried in vacuo (50° C., 3 mm Hg) to give methyl 4-[5-(4-cyanophenoxy)-pentoxy]-3-methoxybenzoate, mp 105°–107° C., HPLC indicating a purity of 99.8%.

Methyl 4-[5-(4-cyanophenoxy)-pentoxy]-3-methoxybenzoate (3600 g, 9.74 mol) is dissolved in tetrahydrofuran (36 L) with warming to 30° C. The solution is then cooled to 20° C. and a solution of tetrabutylammonium hydroxide (40% in water, 7.1 L, 1.64 m) is added over 20 minutes. The reaction mixture is then stirred at an internal temperature of 25° C. for 7 hours and overnight at room temperature (23° C.). After cooling to 10° C. with an ice bath, hydrochloric acid (1.0 N, 14.4 L) is added over 1 hour. After stirring and cooling to 10° C. for three hours, the product is filtered, washed with water (24 L) and dried in vacuo (76° C., 3 mm Hg) to give 4-[5-(4-cyanophenoxy)pentoxy]-3-methoxybenzoic acid, mp 159°–161° C. HPLC indicates 99.1% purity. A second crop of acid is obtained from the flitrates after diluting further with water (20 L). The product is filtered, washed with water (4×3 L) and dried in vacuo to give 4-[5-(4-cyanophenoxy)pentoxy]-3-methoxybenzoic acid, mp 158°–160° C., (HPLC indicates 98.3% purity).

4-[5-(4-cyanophenoxy)pentoxy]-3-methoxybenzoic acid (3600 g, 10.13 mol) is suspended in dichloromethane (36 L) and to this is added thionyl chloride (1345 g, 11.30 mol) dropwise over 20 minutes followed by dimethylformamide (74.4 g, 10.0 mmol). The reaction mixture is stirred at room temperature for 21 hours; after 6 hours a complete solution is obtained. The solution is concentrated in vacuo (50° C, 3 mm Hg) to give 4-[5-(4-cyanophenoxy)pentoxy]-3-methoxybenzoyl chloride as a solid, which is then redissolved in dichloromethane (36 L) without further purification and cooled to 5° C. with an ice bath. Diisopropylamine (3077 g, 30.40 mmol) is added dropwise over a period of 1 hour. The reaction mixture is stirred at 20° C. for 3 hours and then, N,N-dimethylethylenediamine (80.3 g, 0.91 mmol) is added. The reaction is followed by TLC (2:1 ethyl acetate/hexanes, silica plates) until no more byproduct (bis-anhydride of 4-[5-(4-cyanophenoxy)pentoxy]3-methoxybenzoic acid) is detected. The reaction mixture is then stirred overnight at room temperature. Water (18 L) is added, stirred and the layers separated. The organic layer is washed with hydrochloric acid (1.0 N, 23 L), water (18 L), ammonium hydroxide (0.5 N, 2×23 L), water (18 L) and brine solution (18 L). The separated dichloromethane solution is dried over anhydrous magnesium sulfate, filtered and concentrated in vacuo (50° C., 3 mm Hg) to give 4-[5-(4-cyanophenoxy)pentoxy]-3-methoxy-N,N-bis(1-methylethyl)- benzamide as a solid. The solid is dissolved in 2 B ethanol (21.5 L) by warming and to the solution is added water (8.6 L). The product is allowed to crystallize overnight in an ice bath. The product is filtered, washed with EtOH/H$_2$O (5:2, 2×2 L) and dried in vacuo (54° C., 3 mm Hg) to give 4-[5-(4-cyanophenoxy)pentoxy]-3-methoxy-N,N-bis(1-methylethyl)- benzamide, mp 90°–92° C. HPLC indicates a purity of >99.7%.

Ethanol (2B,6.0 L) is cooled in an ice bath to 0° C. and saturated with anhydrous hydrogen chloride over a period of 7 ½hours. The solution is left in the ice bath overnight and the hydrogen chloride addition is continued an additional hour at 0° C. 4-[5-(4-Cyanophenoxy)-pentoxy]-3-methoxy-N,N-bis(1-methylethyl)- benzamide (4200 g, 9.57 mole) is added rapidly over 30 minutes and an exotherm raises the reaction mixture temperature to 10° C. Hydrogen chloride addition is continued for 6 hours and the purple solution stirred overnight at 20° C. The reaction mixture is followed by TLC (ethyl acetate/hexane, 2:1) using silica plates. A total of 4–5 days is required for completion of this reaction with periodic resaturation with hydrogen chloride. The thick purple solution is transferred into a 20 gallon reactor and triturated with anhydrous diethyl ether (2×30 L), removing the ether solution after each wash. The reactor is put under vacuum (3 mm Hg) for 0.5 hour to dispel most of the hydrogen chloride leaving ethyl 4-[5-[3-methoxy-4-[N,N-bis(1-methylethyl)aminocarbonyl]-phenoxy]pentoxy]benzenecarboximidoate monohydrochloride as a thick purple oil.

Ethanol 2 B (42 L) is added to the reactor and the ethyl 4-[5-[3-methoxy-4-[N,N-bis(1-methylethyl)aminocarbonyl]phenoxy]-pentoxy]benzenecarboximidoate monohydrochloride is dissolved. The solution is cooled to 5° C. and anhydrous ammonia is bubbled into the solution for 7.5 hours until saturation is obtained. After stirring overnight in the ice bath, and ammonia addition is continued another 7.5 hours at 5° C. The reaction mixture is followed by TLC (CH$_2$Cl$_2$/MeOH, 9:1) using silica plates. A total of four days is required for completion of reaction with periodic resaturation with ammonia gas. The reaction mixture is filtered and the filtrate divided into two equal portions. Concentration in vacuo (55° C., 3 mm Hg) gives an oily viscous suspension which is charged into a 20 gallon reactor. This is admixed with hydrochloric acid (12 N, 560 ml), diluted with water (44 L). At this point, the compound dissolves (pH is 1.62). The solution is washed with diethyl ether (3×18 L), and the pH adjusted to 12.6 with a 6 N sodium hydroxide solution (3.0 L). The oily suspension crystallizes after stirring overnight at 20° C. The product is filtered, washed with water (5×4 L) and dried in vacuo (60° C. 3 mm Hg) to give the product. The second half of the reaction mixture is worked up in a similar manner to give 4-[5-[4-(aminoiminomethyl)phenoxy]pentoxy]-3-methoxy-N,N-bis(1-methylethyl)-benzamide is obtained, mp 112°–114° C. HPLC indicates a purity of 98.5%.

EXAMPLE 8

A stirred, 0° C. solution of 4-[5-[4-(aminoiminomethyl)phenoxy]pentoxy]-3-methoxy-N,N-bis(1-methylethyl)benzamide monohydrochloride (200 mg, 0.41 mmol) in 4.0 mL anhydrous methylene chloride is treated sequentially with triethylamine (0.068 mL, 0.48 mmol) and methyl isocyanate (0.030 mL, 0.49 mmol). The solution is stirred 30 minutes, concentrated in vacuo and the resulting solids are partitioned between ethyl acetate and water. The organic layer is washed with water and brine, dried over sodium sulfate and concentrated. The resulting material is purified by chromatography on silica gel (15 g) with 70–100% ethyl acetate/hexanes as the eluent to afford 4-[5-[4-[amino(-methylaminocarbonylimino)methyl]phenoxy]pentoxy]-3-methoxy-N,N-bis(1-methylethyl)benzamide as a colorless foam;

CHN calculated for $C_{28}H_{40}N_4O_5$: Theory: % C: 65.60; % H: 7.87; % N: 10.93; Found: % C: 65.79; % H: 7.61; % N: 10.90.

EXAMPLE 9

In a way analogously as described, for example, in example 8, the following compounds can be manufactured: 4-[5-[4-[Amino[(3,4-dimethoxyphenyl)carbonylimino]ethyl ]phenoxy]pentoxy]-3-methoxy-N,N-bis(1-methylethyl)benzamide is obtained from 4-[5-[4-(aminoiminomethyl)phenoxy]pentoxy]-3-methoxy-N,N-his(1-methylethyl)benzamide monohydrochloride (400 mg) and 3,4-dimethoxybenzoyl chloride (170 mg) as a colorless foam;

CHN calculated for $C_{35}H_{45}N_3O_7$: Theory: % C: 67.83; % H: 7.32; % N: 6.78; Found: % C: 68.19; % H: 7.55; % N: 6.23.

4-[5-[4-[Amino[[[(1-methylethyl)amino]carbonyl]imino)methyl]phenoxy]pentoxy]-3-methoxy-N,N-bis(1-methylethyl)benzamide is obtained from 4-[5-[4-(aminoiminomethyl)phenoxy]pentoxy 1-3-methoxy-N,N-bis(1-methylethyl)benzamide monohydrochloride (300 mg) and isopropyl isocyanate (54 mg) as a colorless foam:

CHN calculated for $C_{30}H_{44}N_4O_5$: Theory: % C: 66.64; % H: 8.20; % N: 10.36; Found: % C: 66.94; % H: 8.09; % N: 9.99.

4-[5-[4-[(Ethylamino)carbonyl]imino]aminomethyl]-phenoxy]pentoxy]-3-methoxy-N,N-bis(1-methylethyl)-benzamide is obtained from 4-[5-[4-(aminoiminomethyl)phenoxy]pentoxy]-3-methoxy-N,N-his(1-methylethyl)benzamide monohydrochloride (300 mg) and ethyl isocyanate (45 mg) as a colorless foam:

CHN calculated for $C_{29}H_{42}N_4O_5$; Theory: % C: 66.13; % H: 8.0; % N: 10.64; Found: % C: 66.35; % H: 7.96; % N: 10.25.

4-[5-[4-[Amino[[(phenylamino)carbonyl]imino]methyl]phenoxy]pentoxy]-3-methoxy-N,N-bis(1-methylethyl)benzamide (240 mg) is obtained from 4-[5-[4-(aminoiminomethyl)phenoxy]pentoxy]-3-methoxy-N,N-bis(1-methylethyl)benzamide monohydrochloride (300 mg) and phenyl isocyanate (76 mg) as a colorless foam:

CHN calculated for $C_{33}H_{42}N_4O_5$; Theory: % C: 68.97; % H: 7.37; % N: 9.75; Found: % C: 69.20; % H: 7.75; % N: 9.37.

EXAMPLE 10

In a way analogously as described, for example, in one of the preceeding examples, the following compounds can be manufactured:

4-[5-[4-(aminoiminomethyl)phenoxy]pentoxy]-N-ethyl-N-phenylbenzamide monohydrochloride;

4-[5-[4-(aminoiminomethyl)phenoxy]pentoxy]-2,6-dimethoxy-N,N-bis(1-methylethyl)benzamide monohydrochloride;

4-[5-[4-(aminoiminomethyl)phenoxy]pentoxy]-3,5-dimethoxy-N,N-bis(1-methylethyl)benzamide monohydrochloride;

4-[5-[4-(aminoiminomethyl)phenoxy]pentoxy]-2,3-dimethoxy-N,N-bis(1-methylethyl)benzamide monohydrochloride;

4-[5-[4-(aminoxminomethyl)phenoxy]pentoxy]-3,5-dichloro-N,N-bis(1-methylethyl)benzamide monohydrochloride;

4-[5-[4-(aminoiminomethyl)phenoxy]pentoxy]-2-methoxy-6-methyl-N,N-bis(1-methylethyl)benzamide monohydrochloride;

4-[5-[4-(aminoiminomethyl)phenoxy]pentoxy]-3-chloro-N,N-bis(1-methylethyl)benzamide monohydrochloride;

4-[5-[4-(aminoiminomethyl)phenoxy]pentoxy]-3-bromo-N,N-bis(1-methylethyl)benzamide monohydrochloride;

5-[5-[4-(aminoiminomethyl)phenoxy]pentoxy]-2-methoxy-N,N -bis(1-methylethyl)bezamide monohydrochloride;

5-[5-[4-(aminoiminomethyl)phenoxy]pentoxy]-2-bromo-N,N-bis(1-methylethyl)benzamide monohydrochloride;

4-[5-[4-[(3-pyridylcarbonylamino)iminomethyl]phenoxy]pentoxy]- 3methoxy-N,N-bis(1-methylethyl)benzamide;

4-[5-[4-[(4-pyridylcarbonylamino)iminomethyl]phenoxy]pentoxy]-3-methoxy-N,N-bis(1-methylethyl)benzamide;

4-[5-[4-[1-imidazolylcarbonylamino)iminomethyl]-phenoxy]pentoxy]-3-methoxy-N,N-bis(1-methylethyl)benzamide.

4-[5-[(4-aminoiminomethyl)phenoxy]pentoxy 1-N-(1-methylethyl)-N-(2-pyridyl)-benzamide di-methanesulfonate, m.p. 148°–151°.

EXAMPLE 11

A stirred, 0° C. solution of ethyl 5-[5-(4-cyanophenoxy)pentyloxy]-2-[N-(1-methylethyl)-N-phenylaminocarbonyl]phenoxyacetate (200 mg, 0.44 mmol) in 2.0 mL of anhydrous dichloromethane and 150 mL of anhydrous ethanol at 0° C. is treated with anhydrous hydrogen chloride gas over 30 minutes. This solution is stirred at room temperature for 20 hours and the resulting solution is concentrated in vacuo. The resulting ethyl 4-[5-[3-ethoxycarbonylmethoxy-4-[N-(1-methylethyl)-N-phenyl-aminocarbonyl]phenoxy]pentyloxy]benzenecarboximidoate monohydrochloride is then dissolved in 50 mL of anhydrous ethanol in a pressure tube, and treated with anhydrous ammonia for 5 minutes at 0° C. The pressure tube is sealed and heated to 100° C. for 1 hour. Upon cooling and concentrating in vacuo, the resulting material is purified by chromatography on silica gel (15 g) with 5–20% methanol/dichloromethane as the eluent to afford 4-[5-[4-(aminoiminomethyl)phenoxy]pentyloxy]-2-carbamoylmethoxy-N-(1-methylethyl)-N-phenylbenzamide monohydrochloride as colorless foam; CHN calculated for $C_{30}H_{37}ClN_4O_5$—0.5 $H_2O$:

Theory: % C: 62.33; % H: 6.63; % N: 9.69; Found: % C: 62.05; % H: 6.68; % N: 9.54.

The starting material, ethyl 5-15-(4-cyanophenoxy)-pentyloxy]-2-[N-(1-methylethyl)-N-phenylaminocarbonyl]phenoxyacetate, can be prepared, for example, as follows:

A stirred solution of 2,4-dimethoxybenzoic acid (4.31 g, 23.7 mmol) in 35 mL of dichloromethane is treated with N-isopropylaniline (3.07 mL, 21.33 mmol), hydroxybenzotriazole (3.2 g, 23.7 mmol), and 1-ethyl-3-[3-(dimethylamino)propyl]-carbodiimide hydrochloride (4.54 g, 23.7 mmol). This solution is stirred at room temperature for 18 hours and the resulting solution is partitioned between ethyl acetate and 1N hydrochloride solution. The organic layer is washed with water, dried over sodium sulfate and concentrated. The resulting material is purified by chromatography on silica gel (150 g) with 40–60% ethyl acetate/hexane as the eluent to afford 2,4-dimethoxy-N-(1-methylethyl)-N-phenylbenzamide as a colorless foam.

A stirred solution of 2,4-dimethoxy-N-(1-methylethyl)-N-phenylbenzamide (2.4 g, 8.03 mmol) in 10 ml of dichloromethane at 0° C. was treated with 1N boron tribromide (33.2 mL, 33.2 mmol) and stirred at room temperature for 1 hour. The reaction is poured in to the ice water. After stirring for 15 minutes, the reaction was partitioned between ethyl acetate and brine, dried over magnesium sulfate and concentrated in vacuo to afford yellow foam. This material is purified by chromatography on silica gel (70 g) with 3–5% methanol/dichloromethane as the eluent to afford 2,4-dihydroxy-N-(1-methylethyl)-N-phenylbenzamide as colorless foam.

A stirred solution of 2,4-dihydroxy-N-(1-methylethyl)-N-phenylbenzamide (358 mg, 1.32 mmol) in 6 mL of N,N-dimethylformamide is treated with cesium carbonate (520 mg, 1.58 mmol), and 5-(4-cyanophenoxy)-pentyl bromide (354 mg, 1.32 mmol) and stirred at 40° C. for 24 hours. The reaction is partitioned between ethyl acetate and water, dried over sodium sulfate and concentrated in vacuo to afford a yellow foam. This material is purified by chromatography on silica gel (30 g) with 30–70% ethyl acetate/hexane as the eluent to afford 4-[5-(4-cyanophenoxy)pentyloxy]-2-hydroxy-N-(1-methylethyl)-N-phenylbenzamide as colorless foam.

A stirred solution of 4-[5-(4-cyanophenoxy)pentyloxy]-2-hydroxy-N-(1-methylethyl)-N-phenylbenzamide (250 mg, 0.55 mmol) in 2.5 mL of N,N-dimethylformamide is treated with 60% sodium hydride (22 mg, 0.55 mmol), and ethyl bromoacetate (67 μL, 0.60 mmol) and heated at 70° C. for 2.5 hours. The reaction is partitioned between ethyl acetate and water, dried over sodium sulfate and concentrated in vacuo to afford a yellow foam. This material is purified by chromatography on silica gel (30 g) with 50–70% ethyl acetate/hexane as the eluent to afford ethyl 5-[5-(4-cyanophenoxy)-pentyloxyl-2-[N-(1-methylethyl)-N-phenylaminocarbonyl]phenoxyacetate as colorless foam.

EXAMPLE 12

A stirred, 0° C. solution of ethyl 4-[5-[3-ethoxycarbonylmethoxy-4-[N,N-bis(1-methylethyl)aminocarbonyl]phenoxy]pentyloxy]benzenecarboximidoate monohydrochloride (400 mg, 0.68 mmol) in 25 mL of anhydrous ethanol is treated with 1.36 mL of 1.0N aqueous sodium hydroxide. After stirring 1.5 hours, the reaction is concentrated in vacuo. The resulting 5-[5-[4-(ethoxyiminomethyl)phenoxy]pentyloxy]-2-[N,N-bis(1-methylethyl)carbamoyl]phenoxyacetic acid is then dissolved in 50 mL of anhydrous ethanol in a pressure tube, and treated with ammonium chloride (500 mg, 9.4 mmol). This mixture is treated with anhydrous ammonia for 2 minutes at 0° C. The pressure tube is sealed and heated to 50° C. for 1 hour. Upon cooling and concentrating in vacuo, the resulting material is purified by chromatography on silica gel (15 g) with 20–30% methanol/dichloromethane as the eluent to afford a colorless foam. The resulting 5-[5-[4-(aminoiminomethyl)-phenoxylpentyloxy]-2-[N,N-bis(1-methylethyl)carbamoyl]phenoxyacetic acid monohydrochloride is then dissolved in 150 mL of anhydrous ethanol at 0° C. and treated with anhydrous hydrogen chloride gas over 30 minutes. This solution is stirred at room temperature for 20 hours and the resulting solution is concentrated in vacuo. The resulting material is purified by chromatography on silica gel (15 g) with 5–20% methanol/dichloromethane as the eluent to afford ethyl 5-I 5-[4-(aminoiminomethyl)phenoxylpentyloxyl-2-[N,N-bis(1-methylethyl)carbamoyl]phenoxyacetate monohydrochloride as colorless foam; CHN calculated for $C_{29}H_{42}ClN_3O_6$—1.0 $H_2O$:

Theory: % C: 59.83; % H: 7.62; % N: 7.22; Found: % C: 59.92; % H: 7.22; % N: 7.37.

The starting material, ethyl 4-[5-[3-ethoxycarbonylmethoxy-4-[N,N-bis(1-methylethyl)aminocarbonyl]-phenoxy]pentyloxy]benzenecarboximidoate monohydrochloride, can be prepared, for example, as follows:

A stirred solution of 2,4-dimethoxybenzoyl chloride (10.0 g, 50 mmol) in 10 mL of dichloromethane at 0° C. is treated with 30 mL of diisopropylamine. This solution is stirred at room temperature for 1 hour and the resulting solution is partitioned between ethyl acetate and water. The organic layer is washed with 1N hydrochloride solution, 1N sodium hydroxide solution, water and brine, dried over sodium sulfate and concentrated in vacuo to give 2,4-dimethoxy-N,N-bis(1-methylethyl)-benzamide.

A solution of 2,4-dimethoxy-N,N-bis(1-methylethyl)-benzamide (3.0 g, 11.0 mmol) in 10 ml of dichloromethane at 0° C. is treated with 1N boron tribromide (33.0 mL, 33.0 mmol) and stirred at room temperature for 2 hours. The reaction is concentrated in vacuo, dissolved in 1N sodium hydroxide solution, and acidified with 1N hydrochloric acid to generate solid which is filtered to afford 2,4-dihydroxy-N,N-bis(1-methylethyl)benzamide as white solid.

A solution of 2,4-dihydroxy-N,N-bis(1-methylethyl)-benzamide (3 g, 12.7 mmol) in 30 mL of N,N-dimethylformamide is treated with cesium carbonate (4.97 g, 15.2 mmol), and 5-(4-cyanophenoxy)pentyl bromide (3.4 g, 12.7 mmol) and stirred at 40° C. for 24 hours. The reaction is partitioned between ethyl acetate and water, dried over sodium sulfate and concentrated in vacuo to afford a yellow foam. This material is purified by chromatography on silica gel (30 g) with 30–70% ethyl acetate/hexane as the eluent to afford 4-[5-(4-cyanophenoxy)pentyloxy]-2-hydroxy-N,N-bis(1-methylethyl)benzamide as colorless foam.

A stirred solution of 4-15-(4-cyanophenoxy)pentyloxy]-2-hydroxy-N,N-bis(1-methylethyl)benzamide (0.5 g, 1.18 mmol) in 10.0 mL of N,N-dimethylformamide is treated with 60% sodium hydride (47 mg, 1.18 mmol) and ethyl bromoacetate (144 μL, 1.3 mmol), and heated at 70° C. for 2.5 hours. The reaction is partitioned between ethyl acetate and water, dried over sodium sulfate and concentrated in vacuo to afford yellow foam. The resulting ethyl 5-[5-(4-cyanophenoxy)pentyloxy]-2-[N,N-bis(1-methylethyl)aminocarbonyl]phenoxyacetate in 50 mL of anhydrous ethanol at 0° C. is treated with anhydrous hydrogen chloride gas over 30 minutes. This solution is stirred at room temperature for 20 hours and concentrated in vacuo. This material is purified by chromatography on silica gel with 60% ethyl acetate/hexane as the eluent to afford ethyl 4-[5-[3-ethoxycarbonylmethoxy-4-[N,N-bis( 1-methylethyl)aminocarbonyl]phenoxy]pentyloxy]benzenecarboximidoate monohydrochloride as colorless foam.

EXAMPLE 13

A stirred, refluxing mixture of 4-[5-(4-cyanophenoxy)pentyloxy]-2-hydroxy-N,N-bis(1-methylethyl)benzamide (0.5 g, 1.18 mmol), sodium hydroxide (480 mg, 1.2 mmol), and 50 mL of acetone is treated with chloroform (125 uL, 1.6 mmol) in 20 mL of acetone. The reaction is refluxed for 4 hours and concentrated in vacuo. The resulting material is partitioned between ethyl acetate and 1N hydrochloric acid. The organic layer is washed with brine, dried over magnesium sulfate and concentrated. The resulting material is purified by chromatography on silica gel (20 g) with 40–100% ethyl acetate/hexane followed by 10% MeOH/ethyl acetate as the eluent to afford 5-[5-[4-cyanophenoxy]pentyloxy]-2-[N,N-bis(1-methylethyl)carbamoyl]phenoxydimethylacetic acid as colorless foam. A stirred, 0° C. solution of 5-[5-[4-cyanophenoxylpentyloxy]-2-[N,N-bis(1-methylethyl)carbamoyl]phenoxydimethylacetic acid (210 mg, 0.411 mmol) in 2.0 mL of anhydrous dichloromethane and 150 mL of anhydrous ethanol at 0° C. is treated with anhydrous hydrogen chloride gas over 30 minutes. This solution is stirred at room temperature for 20 hours and the resulting solution is concentrated in vacuo. The resulting ethyl 4-[5-[3-ethoxycarbonyldimethylmethoxy-4-[N,N-bis(1-methylethyl)aminocarbonyl]phenoxylpentyloxylbenzenecarboximidoate monohydrochloride is then dissolved in 50 mL of anhydrous ethanol in a pressure tube, and treated with anhydrous ammonia for 5 minutes at 0° C. The pressure tube is sealed and heated to 100° C. for 1 hour. Upon cooling and concentrating in vacuo, the resulting material is purified by chromatography on silica gel (15 g) with 5–20% methanol/dichloromethane as the eluent to afford ethyl 5-[5-[4-(aminoiminomethyl)phenoxy]pentyloxyl-2-[N,N-bis(1-methylethyl)carbamoyl]phenoxydimethylacetate monohydrochloride as colorless foam.

CHN calculated for $C_{31}H_{46}ClN_3O_6$—1.25 $H_2O$; Theory: % C: 60.57; % H: 7.95; % N: 6.84: Found: % C: 60.57; % H: 7.92; % N: 6.92.

EXAMPLE 14

In a way analogously as described in the previous examples, the following compounds can be prepared:

4-[5-[4-(Aminoiminomethyl)phenoxy]pentyloxy]-2-(dimethylcarbamoylmethoxy)-N,N-bis(1-methylethyl)-benzamide monohydrochloride is obtained from ethyl 4-[5-[3-(dimethylcarbamoylmethoxy)-4-[N,N-bis(1-methylethyl)aminocarbonyl]phenoxy]pentyloxy]benzenecarboximidoate monohydrochloride as colorless foam; CHN calculated for $C_{29}H_{43}ClN_4O_5$—2.5 $H_2O$; Theory: % C: 57.27; % H: 7.96; % N: 9.21; Found: % C: 57.65; % H: 7.73; % N: 8.88.

The starting alkylating material is α-bromo-N,N-dimethylacetamide.

4-[5-[4-(Aminoiminomethyl)phenoxylpentyloxy]-2-(diethylcarbamoylmethoxy)-N,N-bis(1-methylethyl)-benzamide monohydrochloride is obtained from ethyl 4-[5-[3-(diethylcarbamoylmethoxy)-4-[N,N-bis(1-methylethyl)aminocarbonyl]phenoxy]pentyloxy]benzenecarboximidoate monohydrochloride as colorless foam; CHN calculated for $C_{31}H_{47}ClN_4O_5$—0.5 $H_2O$:

Theory: % C: 62.04; % H: 8.06; % N: 9.33; Found: % C: 61.90; % H: 8.07; % N: 9.25.

The starting alkylating material is α-bromo-N,N-diethylacetamide.

4-[5-[4-(aminoiminomethyl)phenoxy]pentyloxyl-N,N-bis(1-methylethyl)-2-[bis(1-methylethyl)carbamoylm benzamide monohydrochloride is obtained from ethyl 4-[5-[3-Ibis(1-methylethyl)carbamoylmethoxy]-4-[N,N-bis(1-methylethyl)aminocarbonyl]-phenoxy]pentyloxy]benzenecarboximidoate monohydrochloride as colorless foam; CHN calculated for $C_{33}H_{51}ClN_4O_5$—1.0 $H_2O$; Theory: % C: 62.20; % H: 8.38; % N: 8.79; Found: % C: 62.36; % H: 8.05; % N: 8.72.

The starting alkylating material is α-bromo-N,N-diisopropylacetamide.

Ethyl 5-[5-[5-[4-(aminoiminomethyl)phenoxy]pentyloxyl-2-[bis(1-methylethyl)carbamoyl]phenoxy]pentanoate monohydrochloride is obtained from ethyl 4-[5-[3-ethoxycarbonylbutoxy-4-[N,N-bis(1-methylethyl)aminocarbonyl]phenoxy]pentyloxy]benzenecarboximidoate monohydrochloride as colorless foam; CHN calculated for $C_{32}H_{48}ClN_3O_6$:

Theory: % C: 63.40; % H: 7.78; % N: 6.93; Found: % C: 63.02; % H: 7.87; % N: 7.15.

The starting alkylating material is ethyl 5-bromopentanoate.

4-[5-[4-( Aminoiminomethyl)phenoxy]pentyloxy]-2-carbamoylmethoxy-N,N-bis(1-methylethyl)benzamide monohydrochloride is obtained from ethyl 4-[5-[3-ethoxycarbonylmethoxy-4-[N,N-bis(1-methylethyl)aminocarbonyl]phenoxy]pentyloxy]benzenecarboximidoate monohydrochloride as colorless foam; CHN calculated for $C_{27}H_{39}ClN_4O_5$—1.5 $H_2O$:

Theory: % C: 57.69; % H: 7.53; % N: 9.97; Found: % C: 57.64; % H: 7.34; % N: 9.88.

The starting alkylating material is ethyl α-bromoacetate.

4-[5-[4-(Aminoiminomethyl)phenoxy]pentyloxy]-2-hydroxy-N-(1-methylethyl)-N-phenylbenzamide monohydrochloride is obtained from ethyl 4-[5-[3-hydroxy-4-[N-(1-methylethyl)-N-phenyl-aminocarbonyl]phenoxy]pentyloxy]benzenecarboximidoate monohydrochloride as colorless foam; CHN calculated for $C_{28}H_{34}ClN_4O_5$:

Theory: % C: 65.68; % H: 6.69; % N: 8.21; Found: % C: 65.30; % H: 6.92; % N: 7.98.

EXAMPLE 15

A stirred solution of 4-[5-[4-(aminoiminomethyl)-phenoxy]pentyloxy]-3-methoxy-N,N-bis(1-methylethyl)benzamide (40.0 g, 87.7 mmol) in 500 mL anhydrous methylene chloride is treated with phenyl acetate (11.1 mL, 87.7 mmol). The solution is stirred 3 hours, concentrated in vacuo and the resulting liquid is purified by chromatography on silica gel (850 g) with 30% ethyl acetate/hexane as the eluent to afford 4-[5-[4-(acetyliminoaminomethyl)phenoxy]pentyloxy]-3-methoxy-N,N-bis(1-methylethyl)benzamide as a colorless foam; CHN calculated for $C_{28}H_{39}N_3O_5$:

Theory: % C: 67.58; % H: 7.90; % N: 8.44; Found: % C: 67.32; % H: 8.29; % N: 8.28.

EXAMPLE 16

A stirred solution of 4-[5-[4-(aminoiminomethyl)-phenoxy]pentyloxy]-2-hydroxy-N,N-bis(1-methylethyl)benzamide monohydrochloride (220 mg, 0.46 mmol) in 10 mL anhydrous methylene chloride is treated with phenyl acetate (73 uL, 0.51 mmol) and triethylamine (73 uL, 0.51 mmol). The solution is stirred overnight, concentrated in vacuo and the resulting liquid is purified by chromatography on silica gel (15 g) with 80–100% ethyl acetate/hexane as the eluent to afford 4-[5-[4-(acetyliminoaminomethyl)phenoxy]pentyloxy]-2-hydroxy-N,N-bis(1-methylethyl)benzamide as a colorless foam; CHN calculated for $C_{27}H_{37}N_3O_5$—0.5 $H_2O$: Theory: % C: 65.83; % H: 7.78; % N: 8,53; Found: % C: 65.58; % H: 7.63; % N: 8,16.

EXAMPLE 17

In a way analogously as described in the previous two examples, the following compounds can be prepared:

4-[5-[4-[amino(propanoylimino)methyl]phenoxy]pentyloxy]-3-methoxy-N,N-bis(1-methylethyl)benzamide is obtained from 4-[5-[4-(aminoiminomethyl)phenoxy]pentyloxy]-3-methoxy-N,N-bis(1-methylethyl)benzamide as colorless foam; CHN calculated for $C_{29}H_{41}N_3O_5$:

Theory: % C: 68.08; % H: 8.08; % N: 8,21; Found: % C: 67.85; % H: 8.35; % N: 7.95.

4-[5-[4-(Acetyliminoaminomethyl)phenoxy]pentyloxy]-2-carbamoylmethoxy-N,N-bis(1-methylethyl)benzamide is obtained from 4-[5-[4-(aminoiminomethyl)phenoxy]pentyloxy]-2-carbamoylmethoxy-N,N-bis(1-methylethyl)benzamide as colorless foam; CHN calculated for $C_{29}H_{40}N_4O_6$-0.5 $H_2O$:

Theory: % C: 63.37; % H: 7.52; % N: 10.19; Found: % C: 63.41; % H: 7.53; % N: 9.85.

4-[5-[4-(Acetyliminoaminomethyl)phenoxy]pentyloxy]-N,N-bis(1-methylethyl)benzamide is obtained from 4-[5-[4-(aminoiminomethyl)phenoxy]pentyloxy]-N,N-bis(1-methylethyl)benzamide monohydrochloride as colorless foam; CHN calculated for $C_{27}H_{37}N_3O_4$:

Theory: % C: 69.30; % H: 7.86; % N: 8,60; Found: % C: 69.35; % H: 7.98; % N: 8.99.

4-[5-[4-[Amino(propanoylimino)methyl]phenoxy]-pentyloxy]-2-hydroxy-N,N-bis(1-methylethyl)benzamide is obtained from 4-[5-[4-(aminoiminomethyl)-phenoxy]pentyloxy]-2-hydroxy-N,N-bis(1-methylethyl)benzamide monohydrochloride as colorless foam; CHN calculated for $C_{28}H_{39}N_3O_5$—0.5 $H_2O$:

Theory: % C: 66.38; % H: 7.96; % N: 8.29; Found: % C: 66.67; % H: 7.84; % N: 8,03.

4-[5-[4-[amino(butyrylimino)methyl]phenoxy]pentyloxy]-2-hydroxy-N,N-bis(1-methylethyl)benzamide is obtained from 4-[5-[4-(aminoiminomethyl)phenoxy]pentyloxy]- 2-hydroxy-N,N-bis(1-methylethyl)benzamide monohydrochloride as colorless foam; CHN calculated for $C_{29}H_{41}N_3O_5$—1.0 $H_2O$:

Theory: % C: 65.76; % H: 8.18; % N: 7.93; Found: % C: 65.92; % H: 7.98; % N: 7.69.

4-[5-[4-[Amino(propanoylimino)methyl]phenoxy]-pentyloxy]-N,N-bis(1-methylethyl)benzamide is obtained from 4-[5-[4-(aminoiminomethyl)phenoxy]pentyloxy]-N,N-bis(1-methylethyl)benzamide hydrochloride as a colorless solid; CHN calculated for $C_{28}H_{39}N_3O_4$:

Theory: % C: 69.83; % H: 8.16; % N: 8.72; Found: % C: 70.05; % H: 8.23; % N: 8.64.

Ethyl 5-[5-[4-[amino(propanoylimino)methyl]-phenoxy]pentyloxy]-2-[N,N-bis(1-methylethyl)carbamoyl]phenoxydimethylacetate is obtained from ethyl 5-[5-[4-(aminoiminomethyl)phenoxy]pentyloxy]-2-[N,N-bis(1-methylethyl)carbamoyl]phenoxydimethylacetate hydrochloride as a colorless foam; CHN calculated for $C_{34}H_{49}N_3O_7$:

Theory: % C: 65.78; % H: 8.12; % N: 6.77; Found: % C: 65.87; % H: 7.99; % N: 6.62.

EXAMPLE 17a

A stirred solution of 4-[5-[4-(aminoiminomethyl)-phenoxy]pentyloxy]-3-methoxy-N,N-bis(1-methylethyl)benzamide (3.0 g, 7.06 mmol) in 15 mL of dichloromethane is treated with 1-ethyl-3-[3-(dimethylamino)-propyl]-carbodiimide hydrochloride (1.67 g, 8.47 mmol), hydroxybenztriazole (1.14 g, 8.47 mmol), and 2-(benzoyloxymethyl)benzoic acid (1.81 g, 7.06 mmol) and stirred at room temperature over 2 hours. The reaction is concentrated in vacuo and purified by chromatography on silica gel (50 g) with 60% ethyl acetate/hexane as the eluent to afford 4-[5-[4-amino[2-(benzoyloxymethyl)benzoyl]iminomethyl]phenoxy]pentyloxy]-3-methoxy-N,N-bis(1-methylethyl)benzamide as a colorless foam; CHN calculated for $C_{42}H_{47}N_3O_7$:

Theory: % C: 70.92; % H: 6.82; % N: 6.06; Found: % C: 70.77; % H: 6.74; % N: 5.83.

EXAMPLE 18

Amberlite IRA-400 (OH) ion-exchange resin (55.5 g) is added in one portion to a stirred ethanol (120 mL)/methanol (30 mL) solution of 4-[5-[4-(aminoiminomethyl)phenoxy] pentyloxy]-3-methoxy-N,N-bis(1-methylethyl)benzamide monohydrochloride (20 g). After stirring for 20 hours, the resin is removed by filtration. The mother liquor is concentrated at reduced pressure to afford 4-[5-[4-(aminoiminomethyl)-phenoxy]pentyloxy]-3-methoxy-N,N-bis(1-methylethyl)benzamide.

The starting material can be prepared as follows:

Acetic anhydride (72.9 g, 67.4 mL) is added under nitrogen at room temperature to 4-hydroxy-3-methoxybenzoic acid (97.7 g) in xylenes (817 g, 950 mL) while stirring. The stirred mixture is heated to 115°–125° C. and heated at 120°–125° C. for 4 to 20 hours under nitrogen. Part of the liquid is then removed by distillation at about 150° bath temperature to a volume of about 700 ml and the mixture is cooled to room temperature to obtain a slurry of 4-acetoxy-3-methoxybenzoic acid which is again diluted with additional xylenes (224 g, 226 mL). N,N-dimethylformamide (DMF, 1.9 g, 2.0 mL) is added followed by dropwise addition, over 2.5 hours, of oxalyl chloride (90.6 g, 62.2 mL). The reaction mixture is stirred at room temperature for 24 hours to obtain a solution of 4-acetoxy-3-methoxybenzoyl chloride which is used as such in the next step. The xylenes solution is cooled to $-14°$ to $-20°$ C. with a brine solution and diisopropylamine (169 g, 234 mL) is added dropwise over a 45 minute period, at a rate so that the temperature does not exceed 0° C. The reaction mixture is allowed to warm to room temperature and is stirred at room temperature (17°–20° C.) for 21 hours. The resulting slurry is filtered under vacuum, and the filter cake is further slurred with xylenes (430 mL) and filtered.

The combined filtrate (about 1260 mL), containing 4-acetoxy-3-methoxy-N,N-bis(1-methylethyl)-benzamide, is treated at room temperature under nitrogen while stirring with 2-aminoethanol (43.1 g, 42.6 mL) added dropwise over a 5 minute period. The reaction mixture is then heated at 78°–85° for 5 hours. The heat source is removed and water (400 mL) is added slowly over a period of 30 minutes. The stirred slurry is cooled to room temperature and stirring at room temperature is continued for 16 hours. The suspension is cooled to 5° C. and filtered. The resulting solid is washed with xylenes and dried in a vacuum oven at 40°–45° C. for 48 hours to obtain 4-hydroxy-3-methoxy-N,N-bis(1-methylethyl)benzamide; $^1$H-NMR (CDCl$_3$): $\delta$1.10–1.50 (m, 12H), 3.62–3.80 (m, 2H), 3.82 (s, 3H), 6.42–6.70 (m, 1H), 6.72–6.88 (m, 3H).

1-Bromo-5-chloropentane (84.7 g, 60.2 mL) is added to a stirred slurry of 4-hydroxy-3-methoxy-N,N-bis(1-methylethyl)benzamide (109 g) and powdered potassium carbonate (72.1 g) in 2-butanone (805 g, 1099 mL). The reaction mixture is heated at 80° C. for 21 hours with moderate stirring, and the slurry is filtered hot to obtain a 2-butanone solution containing 4-(5-chloropentyloxy)-3-methoxy-N,N-bis(1-methylethyl)benzamide. Sodium iodide (97.8 g) is added. The mixture is heated at 80° C. for 21 hours with moderate stirring, and filtered while hot to obtain a 2-butanone solution of 4-(5-iodopentyloxy-3-methoxy-N,N-bis(1-methylethyl)benzamide. Powdered potassium carbonate (72.1 g) and 4-cyanophenol (67.4 g) are added. After the mixture is stirred moderately for 5 minutes, tris[2-(2-methoxyethoxy)ethyl]amine (3.52 g) is added in one portion and the resulting slurry is heated at 78°–80° C. for 21 hours with moderate stirring. The slurry is cooled to 25°–35° C. and sodium hydroxide (1N, 500 mL) is added. The mixture is stirred for 10 minutes, and the aqueous layer is then separated. The organic layer (ca. 1300 mL) is washed with saturated sodium chloride solution (500 mL), and 940 mL of the solvent is removed by distillation at 115° C. The remaining solution is cooled to 60° C., cyclohexane (1526 mL) is added over a 5 minute period, followed by antistatic agent (ASA-3, 0.17 g). The mixture is heated at 76°–79° C. for 5 minutes and filtered hot under vacuum. The filtrate is heated at 76°–79° C. for 5 minutes, cooled slowly to room temperature and stirred over the weekend. The suspension is then cooled to $-8°–12°$ C. and stirred at this temperature for 1.5 hours. The slurry is filtered, the collected product is washed with 2-butanone (22.2 mL)/cyclohexane (178 mL), and dried at 46°–50° C. for 24 hours to yield 4-[5-(4-cyanophenoxy)pentyloxy-3-methoxy-N,N-bis(1-methylethyl)benzamide. Crude product (144 g) is purified by suspending in 2-butanone (215 mL)/cyclohexane (1218 mL) with antistatic agent, heating at about 80° for 5 minutes, filtering the solution while hot, cooling the filtrate to room temperature, stirring overnight, then cooling to 8°–10° C. and stirring for 1.5 hours at 8°–10° C. The slurry is vacuum filtered, the collected product is washed with 2-butanone/cyclohexane, and dried at 46°–50° in a vacuum oven for 24 hours to obtain pure 4-[5-(4-cyanophenoxy)pentyloxy]-3-methoxy-N,N-bis(1-methylethyl)benzamide; $^1$H-NMR (DMSO): $\delta$5 1.10–1.50 (m, 12H), 1.50–1.65 (m, 2H), 1.75–1.85 (m, 4H), 3.55–3.80 (m, 2H), 3.75 (s, 3H), 3.96 (t, J=6.3 Hz, 2H), 4.08 (t, J=6.5 Hz, 2H), 6.75–6.85 (m, 2H), 6.92–6.98 (d, J=8.7 Hz, 1H), 7.06–7.12 (d, J=8.5 Hz, 2H), 7.72–7.78 (d, J=8.4 Hz, 2H).

4-[5-(4-Cyanophenoxy)pentyloxy]-3-methoxy-N,N-bis(1-methylethyl)benzamide can be converted to 4-[5-[4-(aminoiminomethyl)phenoxy]pentyloxy]-3-methoxy-N,N-bis(1-methylethyl)benzamide monohydrochloride similarly to corresponding steps in e.g. example 7.

EXAMPLE 19 a) Preparation of 10,000 tablets each containing 20 mg of the active ingredient, for example, 4-[5-[4-(aminoiminomethyl)phenoxy]pentoxy 1-3-methoxy-N,N-bis(1-methylethyl)benzamide (Z)-2-butenedioate (1:1):

| active ingredient | 200.00 g |
|---|---|
| Lactose | 2,535.00 g |
| Corn starch | 125.00 g |
| Polyethylene glycol 6,000 | 150.00 g |
| Magnesium stearate | 40.00 g |
| Purified water | q.s. |

Procedure: All the powders are passed through a screen with openings of 0.6 min. The drug substance, lactose, magnesium stearate and half of the starch are mixed in a suitable mixer. The other half of the starch is suspended in 65 ml of water and the suspension added to the boiling solution of the polyethylene glycol in 250 nil of water. The paste formed is added to the powders, which are granulated, if necessary, with an additional amount of water. The granulate is dried overnight at 35° C. broken on a screen with 1.2 mm openings and compressed into tablets, using concave punches uppers bisected.

Analogously tablets are prepared, containing about 10–100 mg of one of the other compounds disclosed and exemplified herein.

b) Preparation of 1,000 capsules each containing 40 mg of the active ingredient, for example, 4-[5-[4-(aminoiminomethyl)phenoxy]pentoxy]-3-methoxy-N,N-bis(1-methylethyl)benzamide (Z)-2-butenedioate (1:1):

| active ingredient | 40.00 g |
|---|---|
| Lactose | 177.00 g |
| Modified starch | 80.00 g |
| Magnesium stearate | 3.00 g |

Procedure: All the powders are passed through a screen with openings of 0.6 mm. The drug substance is placed in a suitable mixer and mixed first with the magnesium stearate, then with the lactose and starch until homogenous. No. 2 hard gelatin capsules are filled with 300 mg of said mixture each, using a capsule filling machine.

Analogously capsules are prepared, containing about 10–100 mg of the other compounds disclosed and exemplified herein.

(c) Preparation of 3000 capsules each containing 25 mg of the active ingredient, for example, 4-[5-[4-(aminoiminomethyl)phenoxy]pentoxy]-3-methoxy-N,N-bis(1-methylethyl)benzamide (Z)-2-butenedioate (1:1):

| Active ingredient | 75.00 g |
|---|---|
| Lactose | 750.00 g |
| Avicel PH 102 (microcrystalline cellulose) | 300.00 g |
| Polyplasdone XL (polyvinylpyrrolidone) | 30.00 g |
| Purified water | q.s. |
| Magnesium stearate | 9.0 g |

The active ingredient is passed through a No. 30 hand screen.

The active ingredient, lactose, Avicel PH 102 and Polyplasdone XL are blended for 15 minutes in a mixer. The blend is granulated with sufficient water (about 500 mL), dried in an oven at 35° C. overnight, and passed through a No. 20 screen.

Magnesium stearate is passed through a No. 20 screen, added to the granulation mixture, and the mixture is blended for 5 minutes in a mixer. The blend is encapsulated in No. 0 hard gelatin capsules each containing an amount of the blend equivalent to 25 mg of the active ingredient.

What is claimed is:

1. A compound of the formula

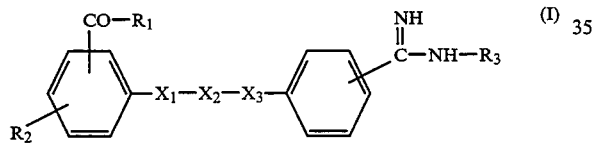

wherein the C(=NH)—NHR$_3$ group may be in tautomeric or isomeric form, $R_1$ is amino which is mono- or disubstituted by a substituent selected from an aliphatic hydrocarbon radical, an araliphatic hydrocarbon radical, an aromatic radical, and a cycloaliphatic hydrocarbon radical, or is amino which is disubstituted by lower alkylene radical or a said radical interrupted by oxygen;

$R_2$ is hydrogen, halogen, trifluoromethyl, an aliphatic hydrocarbon radical, or is hydroxy which is etherified by an aliphatic alcohol, araliphatic alcohol, or aromatic alcohol or which is esterified by an aliphatic or araliphatic carboxylic acid; or $R_2$ is hydroxy; or $R_2$ is hydroxy which is etherified by an aliphatic alcohol which is substituted by carboxy, by esterified carboxy or by amidated carboxy;

$R_3$ is hydrogen or an acyl radical which is derived from an organic carbonic acid, an organic carboxylic acid, a sulfonic acid, or a carbamic acid;

$X_1$ and $X_3$, independently of one another, are oxygen (—O—) or sulphur (—S—); and $X_2$ is a divalent aliphatic hydrocarbon radical which may be interrupted by an aromatic radical;

wherein the phenyl rings of formula I may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein aryl in the above definitions may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein a cycloaliphatic hydrocarbon radical may be substituted by an aliphatic radical; or a pharmaceutically acceptable salt thereof.

2. A compound according to claim 1 wherein $R_1$ is amino which is mono- or disubstituted by a substituent selected from lower alkyl, lower alkenyl, lower alkynyl, phenyl-lower alkyl, phenyl-lower alkenyl, phenyl-lower alkynyl, phenyl, naphthyl, indanyl, fluorenyl, cycloalkyl, and cycloalkenyl, cycloalkyl and cycloalkenyl each being unsubstituted or mono- or polysubstituted by lower alkyl, or is amino which is disubstituted by lower alkylene;

$R_2$ is hydrogen, halogen, trifluoromethyl, lower alkyl, lower alkenyl, lower alkynyl, lower alkoxy, lower alkenyloxy, phenyl-lower alkoxy, phenoxy, lower alkanoyloxy, lower alkenoyloxy, or phenyl-lower alkanoyloxy; or $R_2$ is hydroxy; or $R_2$ is lower alkoxy substituted by carboxy, lower alkoxycarbonyl, aminocarbonyl or mono- or di-lower alkylaminocarbonyl;

$R_3$ is hydrogen, alkoxycarbonyl or alkenyloxycarbonyl, each of which is unsubstituted or substituted by phenyl, naphthyl, indanyl or fluorenyl, or is cycloalkoxycarbonyl being unsubstituted or mono- or polysubstituted by lower alkyl, or is lower alkanoyl or phenyl-lower alkanoyl, or is benzoyl, naphthtoyl, indanoyl or fluorenoyl, or is $C_1$–$C_7$alkanesulfonyl, phenyl-$C_1$–$C_7$alkanesulfonyl, $C_3$–$C_7$-cycloalkanesulfonyl, or phenylsulfonyl, or is aminocarbonyl which is substituted by lower alkyl, phenyl-lower alkyl or phenyl;

$X_1$ and $X_3$, independently of one another, are O or S;

$X_2$ is lower alkylene, lower alkylene-phenylene-lower alkylene or lower alkylene-naphthylene-lower alkylene;

wherein the phenyl rings of formula I may be, independently of one another, substituted by one or more substituents selected from halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy and phenyl-lower alkanoyloxy;

wherein the aromatic radicals in the above definitions may be, independently of one another, substituted by one or more substituents selected from halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy and phenyl-lower alkanoyloxy; or a pharmaceutically acceptable salt thereof.

3. A compound according to claim 1 wherein $R_1$ is amino which is mono- or disubstituted by a substituent selected from $C_1$–$C_7$-alkyl, phenyl-$C_1$–$C_7$-alkyl, phenyl and $C_3$–$C_6$-cycloalkyl, $C_3$–$C_6$-cycloalkyl being unsubstituted or mono- or polysubstituted by $C_1$–$C_7$-alkyl, or is amino which is disubstituted by $C_3$–$C_6$-alkylene;

$R_2$ is hydrogen, $C_1$–$C_7$alkoxy or phenyl-$C_1$–$C_4$-alkoxy; or $R_2$ is hydroxy; or $R_2$ is $C_1$–$C_7$-alkoxy substituted by carboxy or lower alkoxycarbonyl;

$R_3$ is hydrogen, $C_1$–$C_{12}$-alkoxy-carbonyl, $C_2$–$C_5$-alkanoyl, phenyl-$C_2$–$C_5$-alkanoyl, benzoyl which is unsubstituted or substituted by halogen, trifluoromethyl, $C_1$–$C_7$-alkyl, or $C_1$–$C_7$-alkoxy, $C_3$–$C_6$-cycloalkylcarbonyl which is unsubstituted or substituted by $C_1$–$C_7$-alkyl, or is benzoyl, naphthoyl, indanoyl or fluorenoyl, or is $C_1$–$C_7$alkanesulfonyl, phenyl-$C_1$–$C_7$alkanesulfonyl, $C_3$–$C_7$-cycloalkanesulfonyl, or phenylsulfonyl, or is aminocarbonyl which is substituted by $C_1$–$C_7$-alkyl, phenyl-$C_1$–$C_7$alkyl or phenyl;

$X_1$ and $X_3$ each are —O—;

$X_2$ is $C_2$–$C_7$-alkylene or $C_2$–$C_4$-alkylene-phenylene-$C_2$–$C_4$-alkylene;

wherein the phenyl rings of formula I may be unsubstituted or, furthermore, independently of one another, substituted by one or more substituents selected from halogen, trifluoromethyl, $C_1$–$C_7$-alkyl, and $C_1$–$C_7$-alkoxy;

wherein phenyl in the above definitions is unsubstituted or, furthermore, independently of one another, substituted by one or more substituents selected from halogen, trifluoromethyl, $C_1$–$C_7$-alkyl, and $C_1$–$C_7$-alkoxy; or a pharmaceutically acceptable salt thereof.

4. A compound according to claim 1 wherein —CO—$R_1$ is located in position 4 (para) of the corresponding phenyl ring with respect to —$X_1$—; $R_2$— is located in position 2 (ortho) or 3 (meta) of the corresponding phenyl ring with respect to —$X_1$—; and —C(=NH)—NH$R_3$ is located in position 4 (para) of the corresponding phenyl ring with respect to —$X_3$—.

5. A compound according to claim 1 of the formula IA

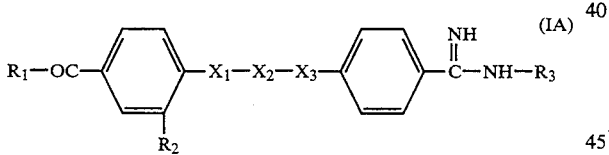

wherein the C(=NH)—NH$R_3$ group may be in tautomeric or isomeric form, $R_1$ is di-$C_1$–$C_4$-alkylamino, $C_1$–$C_4$alkyl-(phenyl)amino, $C_1$–$C_4$alkyl-(phenyl-$C_1$–$C_4$-alkyl)-amino, di-$C_3$–$C_6$-cycloalkylamino which is unsubstituted or substituted by $C_1$–$C_4$-alkyl, or 1-piperidino substituted by $C_1$–$C_4$-alkyl;

$R_2$ is hydrogen, $C_1$–$C_4$-alkoxy, hydroxy, or $C_1$–$C_4$-alkoxy which is substituted by carboxy, lower alkoxycarbonyl, aminocarbonyl or by mono- or di-lower alkylaminocarbonyl;

$R_3$ is hydrogen, $C_1$–$C_{12}$-alkoxycarbonyl, phenyl-$C_1$–$C_4$-alkoxycarbonyl, $C_2$–$C_5$-alkanoyl, benzoyl which is unsubstituted or substituted by halogen, trifluoromethyl, $C_1$–$C_4$-alkyl or by $C_1$–$C_4$-alkoxy, or $C_3$–$C_6$-cycloalkylcarbonyl which is unsubstituted or substituted by $C_1$–$C_4$-alkyl;

X1 and $X_3$ are —O—;

$X_2$ is $C_4$–$C_7$-alkylene;

wherein the phenyl rings of formula IA may be unsubstituted or, furthermore, independently of one another, substituted by one or more substituents selected from halogen, trifluoromethyl, $C_1$–$C_4$-alkyl and $C_1$–$C_4$-alkoxy; or a pharmaceutically acceptable salt thereof.

6. A compound according to claim 5 wherein $R_2$ is hydrogen or $C_1$–$C_4$-alkoxy, and $X_2$ is pentylene.

7. A compound according to claim 5 wherein $R_1$ is di-$C_1$–$C_4$-alkylamino;

$R_2$ is hydrogen or $C_1$–$C_4$-alkoxy;

$R_3$ is hydrogen or $C_2$–$C_5$-alkanoyl;

$X_1$ and $X_3$ are —O—;

$X_2$ is $C_4$–$C_7$-alkylene; or a pharmaceutically acceptable salt thereof.

8. A compound according to claim 7 wherein $R_1$ is di-$C_1$–$C_4$-alkylamino; $R_2$ is $C_1$–$C_4$-alkoxy; $R_3$ is hydrogen; $X_1$ and $X_3$ are —O—; and $X_2$ is pentylene; or a pharmaceutically acceptable salt thereof.

9. A compound according to claim 1 of formula IB

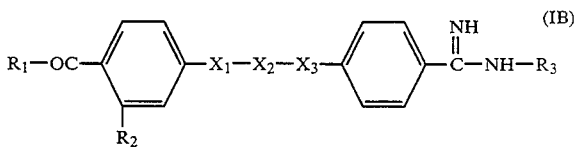

wherein the C(=NH)—NH$R_3$ group may be in tautomeric or isomeric form, $R_1$ is di-$C_1$–$C_4$-alkylamino, $C_1$–$C_4$-alkyl-(phenyl)-amino, $C_1$–$C_4$-alkyl-(phenyl-$C_1$–$C_4$-alkyl)-amino, di-$C_3$–$C_6$-cycloalkylamino which is unsubstituted or substituted by $C_1$–$C_4$-alkyl, or 1-piperidino substituted by $C_1$–$C_4$-alkyl;

$R_2$ is hydrogen or $C_1C_4$-alkoxy; or $R_2$ is hydroxy; or $R_2$ is $C_1$–$C_4$-alkoxy which is substituted by carboxy, lower alkoxycarbonyl, aminocarbonyl or by mono- or di-lower alkylaminocarbonyl;

$R_3$ is hydrogen, $C_1$–$C_{12}$-alkoxycarbonyl, phenyl-$C_1$–$C_4$-alkoxycarbonyl, $C_2$–$C_5$-alkanoyl, benzoyl which is unsubstituted or substituted by halogen, trifluoromethyl, $C_1$–$C_4$-alkyl or by $C_1$–$C_4$-alkoxy, or $C_3$–$C_6$-cycloalkylcarbonyl which is unsubstituted or substituted by $C_1$–$C_4$-alkyl;

$X_1$ and $X_3$ are —O—;

$X_2$ is $C_4$–$C_7$-alkylene;

wherein the phenyl rings of formula IB may be unsubstituted or, furthermore, independently of one another, substituted by one or more substituents selected from halogen, trifluoromethyl, $C_1$–$C_4$-alkyl, and $C_1$–$C_4$-alkoxy; or a pharmaceutically acceptable salt thereof.

10. A compound according to claim 9 wherein $R_1$ is di-$C_1$–$C_4$-alkylamino, $C_1$–$C_4$-alkyl-phenylamino, $C_1$–$C_4$-alkyl-phenyl-$C_1$–$C_4$-alkyl-amino, di-$C_3$–$C_6$-cycloalkylamino which is unsubstituted or substituted by $C_1$–$C_4$-alkyl, or 1-piperidino substituted by $C_1$–$C_4$-alkyl;

$R_2$ is hydrogen, hydroxy or $C_1$–$C_4$-alkoxy; or $R_2$ is $C_1$–$C_a$-alkoxy substituted by $C_1$–$C_4$-alkoxycarbonyl, or by aminocarbonyl;

$R_3$ is hydrogen or $C_2$–$C_5$-alkanoyl;

$X_1$ and $X_3$ are —O—;

$X_2$ is $C_4$–$C_7$-alkylene; or a pharmaceutically acceptable salt thereof.

11. A compound according to claim 9 wherein $R_1$ is di-$C_1$–$C_4$-alkylamino;

$R_2$ is hydrogen, hydroxy, $C_1$–$C_4$-alkoxy, $C_1$–$C_4$-alkoxycarbonylmethoxy or aminocarbonylmethoxy;

$R_3$ is hydrogen or $C_2$–$C_5$-alkanoyl;

$X_1$ and $X_3$ are —O—; and $X_2$ is $C_4$–$C_7$-alkylene; or a pharmaceutically acceptable salt thereof.

12. A compound according to claim 9 wherein $R_2$ is hydroxy, $C_{1-4}$-alkoxycarbonylmethoxy or carbamoylmethoxy, and $X_2$ is pentylene.

13. A compound according to claim 5 which is 4-[5-[4-(aminoiminomethyl)phenoxy]pentoxy]-3-methoxy-N,N-bis(1-methylethyl)benzamide or a pharmaceutically acceptable salt thereof.

14. A compound according to claim 5 which is 4-[5-[4-(aminoiminomethyl)phenoxy]pentoxy]-N,N-bis(1-methylethyl)benzamide or a pharmaceutically acceptable salt thereof.

15. A compound according to claim 5 which is 4-[5-[4-[(acetylimino)aminomethyl]phenoxy]-3-methoxy-N,N-bis-(1-methylethyl)benzamide or a pharmaceutically acceptable salt thereof.

16. A compound according to claim 9 which is 4-[5-[4-(aminoiminomethyl)phenoxy]pentoxy]-2-hydroxy-N,N-bis(1-methylethyl benzamide or a pharmaceutically acceptable salt thereof.

17. A compound according to claim 9 which is 4-[5-[4-(acetyliminoaminomethyl)phenoxy]pentyloxy]-2-hydroxy-N,N-bis(1-methylethyl)benzamide.

18. A compound according to claim 9 which is ethyl 5-[5-[4-(aminoiminomethyl)phenoxy]pentyloxy]-2-[N,N-bis(1-methylethyl)-carbamoyl]phenoxyacetate or a pharmaceutically acceptable salt thereof.

19. A compound according to claim 9 which is 4-[5-[4-(aminoiminomethyl)phenoxy]pentyloxy]-2-carbamoylmethoxy-N,N-bis(1-methylethyl)-benzamide.

20. A compound according to claim 9 which is 4-[5-[4-(propionyliminoaminomethyl)phenoxy]pentyloxy]-2-hydroxy-N,N-bis(1-methylethyl)benzamide.

21. A compound according to claim 9 which is 4-[5-[4-(acetyliminoaminomethyl)phenoxy]pentyloxy]-N,N-bis(1-methylethyl)-benzamide.

22. A compound according to claim 9 which is ethyl 5-[5-[4-[amino(propanoylimino)methyl]phenoxy]pentyloxy]-2-[N,N-bis(1-methylethyl)carbamoyl]phenoxydimethylacetate.

23. A pharmaceutical composition suitable for antagonizing $LTB_4$ in mammals comprising an effective $LTB_4$ antagonizing amount of a compound of claim 1 and a pharmaceutically acceptable carrier.

24. A method of antagonizing $LTB_4$ activity in mammals which comprises administering to a mammal in need thereof an effective $LTB_4$ antagonizing amount of a compound of claim 1.

* * * * *

UNITED STATES PATENT AND TRADEMARK OFFICE
CERTIFICATE OF CORRECTION

PATENT NO.  : 5,451,700
DATED       : September 19, 1995
INVENTOR(S) : Michael M. Morrissey and Hongsuk Suh It is certified that error appears in the above-identified patent and that said Letters Patent is hereby corrected as shown below:

Column 23, line 44, should read:

tained from ethyl 4- [5- [3- [N,N-diethylaminocarbonyl]-

Column 23, line 52, should read:

ethyl 4- [5- [2- [N,N-diethylaminocarbonyl]phenoxyl]pen-

Signed and Sealed this

Eleventh Day of June, 1996

BRUCE LEHMAN

*Attest:*

*Attesting Officer*   Commissioner of Patents and Trademarks

UNITED STATES PATENT AND TRADEMARK OFFICE
CERTIFICATE OF CORRECTION

PATENT NO. : 5,451,700
DATED : September 19, 1995
INVENTOR(S) : Michael M. Morrissey, et al It is certified that error appears in the above-indentified patent and that said Letters Patent is hereby corrected as shown below:

This certificate supersedes Certificate of Correction issued June 11, 1996, the number was erroneously mentioned and should be deleted since no Certificate of Correction was granted.

Signed and Sealed this

Twenty-fourth Day of September, 1996

Attest:

BRUCE LEHMAN

*Attesting Officer*           *Commissioner of Patents and Trademarks*

UNITED STATES PATENT AND TRADEMARK OFFICE
CERTIFICATE OF CORRECTION

PATENT NO. : 5,451,700

DATED : September 19, 1995

INVENTOR(S) : Michael M. Morrissey and Hongsuk Suh

It is certified that error appears in the above-identified patent and that said Letters Patent is hereby corrected as shown below:

Column 23, line 44, should read:

tained from ethyl 4- [5- [3- [N,N-diethylaminocarbonyl]-

Column 23, line 52, should read:

ethyl 4- [5- [2- [N,N-diethylaminocarbonyl]phenoxyl]pen-

Signed and Sealed this

Fifteenth Day of April, 1997

Attest:

BRUCE LEHMAN

Attesting Officer     Commissioner of Patents and Trademarks